(12) United States Patent
Ertongur-Fauth et al.

(10) Patent No.: US 9,809,853 B2
(45) Date of Patent: Nov. 7, 2017

(54) CALCIUM-ACTIVATED CHLORIDE CHANNEL INVOLVED IN HUMAN SWEAT FORMATION

(71) Applicant: BRAIN Biotechnology Research and Information Network AG, Zwingenberg (DE)

(72) Inventors: Torsten Ertongur-Fauth, Darmstadt (DE); Andreas Hochheimer, Darmstadt (DE); Michael Krohn, Lorsch (DE)

(73) Assignee: Brain Biotechnology Research and Information Network AG, Zwingenberg (DE)

( * ) Notice: Subject to any disclaimer, the term of this patent is extended or adjusted under 35 U.S.C. 154(b) by 0 days.

(21) Appl. No.: 14/422,313

(22) PCT Filed: Aug. 14, 2013

(86) PCT No.: PCT/EP2013/067044
§ 371 (c)(1),
(2) Date: Feb. 18, 2015

(87) PCT Pub. No.: WO2014/027050
PCT Pub. Date: Feb. 20, 2014

(65) Prior Publication Data
US 2015/0240303 A1     Aug. 27, 2015

(30) Foreign Application Priority Data
Aug. 16, 2012   (EP) .................... 12180628

(51) Int. Cl.
*C12P 21/02*     (2006.01)
*C12Q 1/68*      (2006.01)
*C07K 14/705*    (2006.01)

(52) U.S. Cl.
CPC .......... *C12Q 1/6876* (2013.01); *C07K 14/705* (2013.01); *C12Q 2600/106* (2013.01)

(58) Field of Classification Search
None
See application file for complete search history.

(56) References Cited

U.S. PATENT DOCUMENTS

2009/0307791 A1   12/2009   Schroeder et al.

OTHER PUBLICATIONS

Ferrera et al., "Regulation of TMEM16A Chloride Channel Properties by Alternative Splicing", Journal of Biological Chemistry (2009), vol. 284, No. 48, pp. 33360-33368.
Ferrera et al., "A minimal isoform of the TMEM16A protein associated with chloride channel activity", Biochimica et Biophysica Acta (2011), vol. 1808, No. 9, pp. 2214-2223.
Munkonge et al., "Measurement of halide efflux from cultured and primary airway epithelial cells using fluorescence indicators", Journal of Cystic Fibrosis (2004), vol. 3, pp. 171-176.
O'Driscoll et al., "Increased complexity of TMEM16A/Anoctamin 1 transcript alternative splicing", BMC Molecular Biology (2011), vol. 12, No. 1, p. 35 (13 pages).
Servetnyk et al., "Chloride transport in NCL-SG3 sweat gland cells: Channels involved", Experimental and Molecular Pathology (2007), vol. 83, pp. 47-53.
Schroeder et al., Database Accession No. AXT98906 retrieved from EBI (2010) (1 page).
Schroeder et al., Database Accession No. AXT98907 retrieved from EBI (2010) (1 page).
Isogai et al., Database Accession No. DA761912 retrieved from EBI (2005) (1 page).
International Search Report and Written Opinion issued in corresponding Application No. PCT/EP2013/067044, mailed Oct. 25, 2013.
Caputo, A. et al., "TMEMI6A, A Membrane Protein Associated with Calcium-Dependent Chloride Channel Activity", Science, (2008), vol. 322, pp. 590-594.
Clark, C., "Sweating and Hyperhidrosis", The Pharmaceutical Journal, (2006), vol. 276, pp. 757-760.
Darbre, P.O., "Aluminium, Antiperspirants and Breast Cancer", Journal of Inorganic Biochemistry, (2005), vol. 99, pp. 1912-1919.
Eggermont, J., "Calcium-Activated Chloride Channels: (un)known, (un)loved?", Proc Am Thorac Soc, (2004), vol. 1, pp. 22-27.
Ferrera, L. et al., "Regulation of TMEMI6A Chloride Channel Properties by Alternative Splicing", The Journal of Biological Chemistry, (2009), vol. 284, No. 48, pp. 33360-33368.

(Continued)

*Primary Examiner* — Jim Ketter
(74) *Attorney, Agent, or Firm* — Hunton & Williams LLP

(57) ABSTRACT

Accordingly, the present invention relates to a nucleic acid molecule encoding a protein capable of forming a calcium-activated chloride channel, wherein said nucleic acid molecule comprises or consists of (a) a nucleic acid molecule encoding a protein having the amino acid sequence of SEQ ID NO:1; (b) a nucleic acid molecule having the DNA sequence of SEQ ID NO:2; (c) a nucleic acid molecule having the sequence of SEQ ID NO:2, wherein each thymine is replaced by uracil; (d) a nucleic acid molecule that hybridizes under stringent conditions to the complementary strand of a nucleic acid molecule of (a), (b) or (c); (e) a nucleic acid molecule encoding a protein having at least 97% sequence identity to the protein of (a); or (f) a nucleic acid molecule that is degenerate with respect to the nucleic acid molecule of (b), (c) or (d). The present invention further relates to a protein capable of forming a calcium-activated chloride channel, the use of the nucleic acid molecule of or the protein of the invention for identifying an inhibitor of sweat formation as well as an in vitro method of identifying an inhibitor of sweat formation.

13 Claims, 19 Drawing Sheets

(56) References Cited

OTHER PUBLICATIONS

Figure 1:
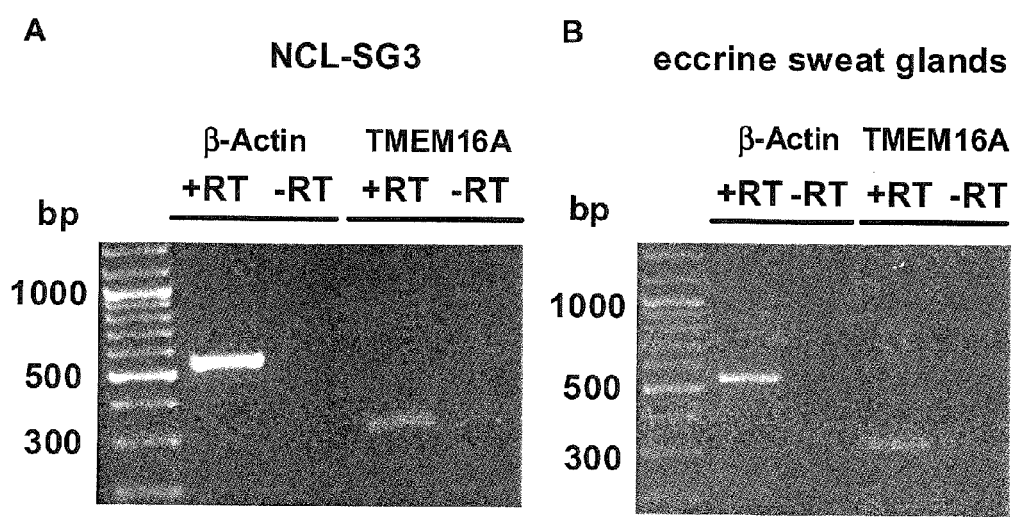

Ferrera, L. et al., "A Minimal Isoform of the TMEMI6A Protein Associated with Chloride Channel Activity", Biochimica et Biophysica Acta, (2011), vol. 1808, pp. 2214-2223.

Galietta, L.J. et al., "Green Fluorescent Protein-Based Halide Indicators with Improved Chloride and Iodide Affinities", FEBS Letters, (2001), vol. 499, pp. 220-224.

Galietta, L.J. et al., "Cell-Based Assay for High-Throughput Quantitative Screening of CFTR Chloride Transport Agonists", American Journal of Physiology, (2001), vol. 281, pp. C1734-C1742.

Galietta, L.J., "The TMEM16 Protein Family: A New Class of Chloride Channels?", Biophysical Journal, (2009), vol. 97, pp. 3047-3053.

Garg, S. et al., "Allergic Contact Dermatitis from Aluminium in Deodorants", Contact Dermatitis, (2010), vol. 62, pp. 57-58.

Hartzell, C. et al., "Calcium-Activated Chloride Channels", Annu. Rev. Physiol, (2005), vol. 67, pp. 719-758.

Hartzell, H.C. et al., "Anoctamin/TMEM16 Family Members are Ca2+-Activated Cl− Channels", J Physiol, (2009), vol. 587, pp. 2127-2139.

Jayaraman, S. et al., "Mechanism and Cellular Applications of a Green Fluorescent Protein-Based Halide Sensor", The Journal of Biological Chemistry, (2000), vol. 275, No. 9, pp. 6047-6050.

Jentsch, T.J. et al., "Molecular Structure and Physiological Function of Chloride Channels", Physiol Rev, (2002), vol. 82, pp. 503-568.

Ko, W.H. et al., "Extracellular ATP can Activate Autonomic Signal Transduction Pathways in Cultured Equine Sweat Gland Epithelial Cells", J Exp Bioi, (1994), vol. 190, 239-252.

Kunzelmann, K. et al., "Bestrophin and TMEM16-Ca(2+) Activated Cl(−) Channels with Different Functions", Cell Calcium, (2009), vol. 46, pp. 233-241.

Lee, C.M. et al., "The Primary Culture of Epithelia from the Secretory Coil and Collecting Duct of Normal Human and Cystic Fibrotic Eccrine Sweat Glands", Journal of Cell Science, (1986), vol. 83, pp. 103-118.

Lee, C.M. et al., "A Human Eccrine Sweat Gland Cell Line that Retains the Capacity for Transepithelial Ion Transport", Journal of Cell Science, (1989), vol. 92 ( Pt 2), pp. 241-249.

Mazzone, A. et al., "Altered Expression of Ano1 Variants in Human Diabetic Gastroparesis", The Journal of Biological Chemistry, (2011), vol. 286, pp. 13393-13403.

Mork, A.C. et al., "cAMP-Induced Chloride Transport in NCL-SG3 Sweat Gland Cells", Acta Physiol Scand, (1996), vol. 157, pp. 21-32.

Nagai, T. et al., "A Variant of Yellow Fluorescent Protein with Fast and Efficient Maturation for Cell-Biological Applications", Nature Biotechnology, (2002), vol. 20, pp. 87-90.

Namer, M. et al., "The Use of Deodorants/Antiperspirants does not Constitute a Risk Factor for Breast Cancer", Bulletin du Cancer, (2008), vol. 95, No. 9, pp. 871-880.

Namkung, W. et al., "TMEMI6A Inhibitors Reveal TMEMI6A as a Minor Component of Calcium-Activated Chloride Channel Conductance in Airway and Intestinal Epithelial Cells", The Journal of Biological Chemistry, (2010), vol. 286, pp. 2365-2374.

Namkung, W et al., "Inhibition of Ca2+-Activated Cl− Channels by Gallotannins as a Possible Molecular Basis for Health Benefits of Red Wine and Green Tea", The FASEB Journal, (2010), vol. 24, pp. 4178-4186.

O'Driscoll, K.E. et al., "Increased Complexity of Tmem16a/ Anoctamin 1 Transcript Alternative Splicing", BMC Molecular Biology, (2011) vol. 12, p. 35.

Ring, A. et al., "Calcium-Activated Chloride Fluxes in Cultured NCL-SG3 Sweat Gland Cells", Cell Biology International (1995), vol. 19, No. 4, pp. 265-278.

Saga, K.; "Structure and Function of Human Sweat Glands Studied with Histochemistry and Cytochemistry", Prog Histochem Cytochem, (2002) vol. 37, pp. 323-386.

Sato, K. et al., "Role of Calcium in Cholinergic and Adrenergic Mechanisms of Eccrine Sweat Secretion", The American Journal of Physiology, (1981), vol. 241, pp. C113-C120.

Sato, K. et al., "Pharmacologic Responsiveness of Isolated Single Eccrine Sweat Glands", The American Journal of Physiology, (1981), vol. 240, pp. R44-R51.

Sato, K., "Differing Luminal Potential Difference of Cystic Fibrosis and Control Sweat Secretory Coils in Vitro", The American Journal of Physiology, (1984), vol. 247, pp. R646-R649.

Sato, K. et al., "Relationship between Quin2-determined Cytosolic [Ca2+] and Sweat Secretion", The American Journal of Physiology, (1988), vol. 254, pp. C310-C317.

Schroeder, B.C. et al., "Expression Cloning of TMEMI6A as a Calcium-Activated Chloride Channel Subunit", Cell, (2008), vol. 134, pp. 1019-1029.

Servetnyk, Z. et al., "Chloride Transport in NCL-SG3 Sweat Gland Cells: Channels Involved", Experimental and Molecular Pathology, (2007), vol. 83, pp. 47-53.

Tester, M., "Techniques for Studying Ion Channels: An Introduction", Journal of Experimental Botany, (1997), vol. 48, Spec Issue, pp. 353-359.

Tian, Y. et al., "Calmodulin-Dependent Activation of the Epithelial Calcium-Dependent Chloride Channel TMEM16A", The FASEB Journal, (2011) vol. 25, pp. 1058-1068.

Verkman, A.S. et al., "Chloride Channels as Drug Targets", Nature Reviews, (2009), vol. 8, pp. 153-171.

Wachter, R.M. et al., "Sensitivity of the Yellow Variant of Green Fluorescent Protein to Halides and Nitrate", Current Biology, (1999), vol. 9, No. 17, pp. R628-R629.

Wachter, R.M. et al., "Crystallographic and Energetic Analysis of Binding of Selected Anions to the Yellow Variants of Green Fluorescent Protein", Journal of Molecular Biology, (2000), vol. 301, pp. 157-171.

Wilson, S.M. et al., "The Regulation of Membrane 125I− and 86Rb+ Permeability in a Virally Transformed Cell Line (NCL-SG3) Derived from the Human Sweat Gland Epithelium", Experimental Physiology, (1994), vol. 79, pp. 445-459.

Wilson, S.M. et al., "Calcium-Dependent Regulation of Membrane Ion Permeability in a Cell Line Derived from the Equine Sweat Gland Epithelium", Comp. Biochem. Physiol. (1995), vol. 111A, No. 2, pp. 215-221.

Worle, B. et al., "Definition and Treatment of Primary Hyperhidrosis", J Dtsch Dermatol Ges, (2007), vol. 5, 625-628.

Xiao, Q. et al., "Voltage- and Calcium-Dependent Gating of TMEM16A/Ano1 Chloride Channels are Physically Coupled by the First Intracellular Loop", Proc Natl Acad Sci USA, (2011) vol. 108, No. 21, pp. 8891-8896.

Yang, Y.D. et al., "TMEM16A Confers Receptor-Activated Calcium-Dependent Chloride Conductance", Nature, (2008), vol. 455, pp. 1210-1215.

Sato, K. et al., "Normal and Abnormal Eccrine Sweat Gland Function", In HP., S.N. a. B. (ed). Pathophysiology of Dermatologic Diseases, McGraw-Hill Inc., pp. 211-234.

A

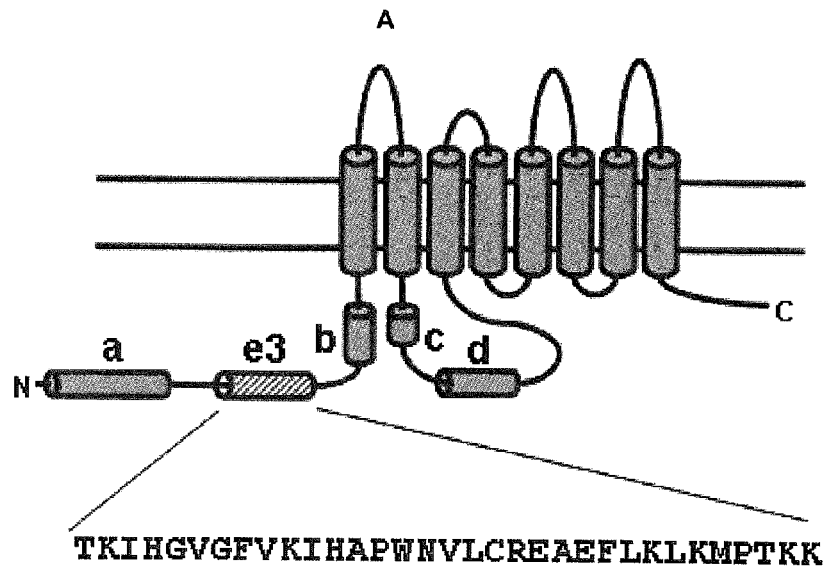

TKIHGVGFVKIHAPWNVLCREAEFLKLKMPTKK

B

```
1   atg agg gtc aac gag aag tac tcg acg ctc ccg gcc gag gac cgc agc
     m   r   v   n   e   k   y   s   t   l   p   a   e   d   r   s
49  gtc cac atc atc aac atc tgc gcc atc gag gac atc ggc tac ctg ccg
     v   h   i   i   n   i   c   a   i   e   d   i   g   y   l   p
97  tcc gag ggc acg ctg ctg aac tcc tta tct gtg gac cct gat gcc gag
     s   e   g   t   l   l   n   s   l   s   v   d   p   d   a   e
145 tgc aag tat ggc ctg tac ttc agg gac ggc cgg cgc aag gtg gac tac
     c   k   y   g   l   y   f   r   d   g   r   r   k   v   d   y
193 atc ctg gtc tac cat cac aag agg ccc tcg ggc aac cgg acc ctg gtc
     i   l   v   y   h   h   k   r   p   s   g   n   r   t   l   v
241 agg agg gtg cag cac agc gac acc ccc tct ggg gct cgc agc gtc aag
     r   r   v   q   h   s   d   t   p   s   g   a   r   s   v   k
289 cag gac cac ccc ctg ccg ggc aag ggg gcg tcg ctg gat gca ggc tcg
     q   d   h   p   l   p   g   k   g   a   s   l   d   a   g   s
337 ggg gag ccc ccg atg gac tac cac gag gat gac aag cgc ttc cgc agg
     g   e   p   p   m   d   y   h   e   d   d   k   r   f   r   r
385 gag gag tac gag ggc aac ctc ctc gag gcg ggc ctg gag ctg gag cgg
     e   e   y   e   g   n   l   l   e   a   g   l   e   l   e   r
```

Figure 3

```
433  gac gag gac act aaa atc cac gga gtc ggg ttt gtg aaa atc cat gcc
      d   e   d   t   k   i   h   g   v   g   f   v   k   i   h   a
481  ccc tgg aac gtg ctg tgc aga gag gcc gag ttt ctg aaa ctg aag atg
      p   w   n   v   l   c   r   e   a   e   f   l   k   l   k   m
529  ccg acg aag aag atg tac cac att aat gag acc cgt ggc ctc ctg aaa
      p   t   k   k   m   y   h   i   n   e   t   r   g   l   l   k
577  aaa atc aac tct gtg ctc cag aaa atc aca gat ccc atc cag ccc aaa
      k   i   n   s   v   l   q   k   i   t   d   p   i   q   p   k
625  gtg gct gag cac agg ccc cag acc atg aag aga ctc tcc tat ccc ttc
      v   a   e   h   r   p   q   t   m   k   r   l   s   y   p   f
673  tcc cgg gag aag cag cat cta ttt gac ttg tct gat aag gat tcc ttt
      s   r   e   k   q   h   l   f   d   l   s   d   k   d   s   f
721  ttc gac agc aaa acc cgg agc acg att gtc tat gag atc ttg aag aga
      f   d   s   k   t   r   s   t   i   v   y   e   i   l   k   r
769  acg acg tgt aca aag gcc aag tac agc atg ggc atc acg agc ctg ctg
      t   t   c   t   k   a   k   y   s   m   g   i   t   s   l   l
817  gcc aat ggt gtg tac gcg gct gca tac cca ctg cac gat gga gac tac
      a   n   g   v   y   a   a   a   y   p   l   h   d   g   d   y
865  aac ggt gaa aac gtc gag ttc aac gac aga aaa ctc ctg tac gaa gag
      n   g   e   n   v   e   f   n   d   r   k   l   l   y   e   e
913  tgg gca cgc tat gga gtt ttc tat aag tac cag ccc atc gac ctg gtc
      w   a   r   y   g   v   f   y   k   y   q   p   i   d   l   v
961  agg aag tat ttt ggg gag aag atc ggc ctg tac ttc gcc tgg ctg ggc
      r   k   y   f   g   e   k   i   g   l   y   f   a   w   l   g
1009 gtg tac acc cag atg ctc atc cct gcc tcc atc gtg gga atc att gtc
      v   y   t   q   m   l   i   p   a   s   i   v   g   i   i   v
1057 ttc ctg tac gga tgc gcc acc atg gat gaa aac atc ccc agc atg gag
      f   l   y   g   c   a   t   m   d   e   n   i   p   s   m   e
1105 atg tgt gac cag aga cac aat atc acc atg tgc ccg ctt tgc gac aag
      m   c   d   q   r   h   n   i   t   m   c   p   l   c   d   k
1153 acc tgc agc tac tgg aag atg agc tca gcc tgc gcc acg gcc cgc gcc
      t   c   s   y   w   k   m   s   s   a   c   a   t   a   r   a
1201 agc cac ctc ttc gac aac ccc gcc acg gtc ttc tct gtc ttc atg
      s   h   l   f   d   n   p   a   t   v   f   f   s   v   f   m
1249 gcc ctc tgg gct gcc acc ttc atg gag cac tgg aag cgg aaa cag atg
      a   l   w   a   a   t   f   m   e   h   w   k   r   k   q   m
```

Figure 3 continued

```
1297  cga ctc aac tac cgc tgg gac ctc acg ggc ttt gaa gag gaa gag gag
       r   l   n   y   r   w   d   l   t   g   f   e   e   e   e   e
1345  gct gtc aag gat cat cct aga gct gaa tac gaa gcc aga gtc ttg gag
       a   v   k   d   h   p   r   a   e   y   e   a   r   v   l   e
1393  aag tct ctg aag aaa gag tcc aga aac aaa gag act gac aaa gtg aag
       k   s   l   k   k   e   s   r   n   k   e   t   d   k   v   k
1441  ctg aca tgg aga gat cgg ttc cca gcc tac ctc act aac ttg gtc tcc
       l   t   w   r   d   r   f   p   a   y   l   t   n   l   v   s
1489  atc atc ttc atg att gca gtg acg ttt gcc atc gtc ctc ggc gtc atc
       i   i   f   m   i   a   v   t   f   a   i   v   l   g   v   i
1537  atc tac aga atc tcc atg gcc gcc gcc ttg gcc atg aac tcc tcc ccc
       i   y   r   i   s   m   a   a   a   l   a   m   n   s   s   p
1585  tcc gtg cgg tcc aac atc cgg gtc aca gtc aca gcc acc gca gtc atc
       s   v   r   s   n   i   r   v   t   v   t   a   t   a   v   i
1633  atc aac cta gtg gtc atc atc ctc ctg gac gag gtg tat ggc tgc ata
       i   n   l   v   v   i   i   l   l   d   e   v   y   g   c   i
1681  gcc cga tgg ctc acc aag atc gag gtc cca aag acg gag aaa agc ttt
       a   r   w   l   t   k   i   e   v   p   k   t   e   k   s   f
1729  gag gag agg ctg atc ttc aag gct ttc ctg ctg aag ttt gtg aat tcc
       e   e   r   l   i   f   k   a   f   l   l   k   f   v   n   s
1777  tac acc ccc atc ttt tac gtg gcg ttc ttc aaa ggc cgg ttt gtt gga
       y   t   p   i   f   y   v   a   f   f   k   g   r   f   v   g
1825  cgc ccg ggc gac tac gtg tac att ttc cgt tcc ttc cga atg gaa gag
       r   p   g   d   y   v   y   i   f   r   s   f   r   m   e   e
1873  tgt gcg cca ggg ggc tgc ctg atg gag cta tgc atc cag ctc agc atc
       c   a   p   g   g   c   l   m   e   l   c   i   q   l   s   i
1921  atc atg ctg ggg aaa cag ctg atc cag aac aac ctg ttc gag atc ggc
       i   m   l   g   k   q   l   i   q   n   n   l   f   e   i   g
1969  atc ccg aag atg aag aag ctc atc cgc tac ctg aag ctg aag cag cag
       i   p   k   m   k   k   l   i   r   y   l   k   l   k   q   q
2017  agc ccc cct gac cac gag gag tgt gtc aag agg aaa cag cgg tac gag
       s   p   p   d   h   e   e   c   v   k   r   k   q   r   y   e
2065  gtg gat tac aac ctg gag ccc ttc gcg ggc ctc acc cca gag tac atg
       v   d   y   n   l   e   p   f   a   g   l   t   p   e   y   m
2113  gaa atg atc atc cag ttt ggc ttc gtc acc ctg ttt gtc gcc tcc ttc
       e   m   i   i   q   f   g   f   v   t   l   f   v   a   s   f
2161  ccc ctg gcc cca ctg ttt gcg ctg ctg aac aac atc atc gag atc cgc
       p   l   a   p   l   f   a   l   l   n   n   i   i   e   i   r
```

Figure 3 continued

```
2209  ctg gac gcc aaa aag ttt gtc act gag ctc cga agg ccg gta gct gtc
       l   d   a   k   k   f   v   t   e   l   r   r   p   v   a   v
2257  aga gcc aaa gac atc gga atc tgg tac aat atc ctc aga ggc att ggg
       r   a   k   d   i   g   i   w   y   n   i   l   r   g   i   g
2305  aag ctt gct gtc atc atc aat gcc ttc gtg atc tcc ttc acg tct gac
       k   l   a   v   i   i   n   a   f   v   i   s   f   t   s   d
2353  ttc atc ccg cgc ctg gtg tac ctc tac atg tac agt aag aac ggg acc
       f   i   p   r   l   v   y   l   y   m   y   s   k   n   g   t
2401  atg cac ggc ttc gtc aac cac acc ctc tcc tcc ttc aac gtc agt gac
       m   h   g   f   v   n   h   t   l   s   s   f   n   v   s   d
2449  ttc cag aac ggc acg gcc ccc aat gac ccc ctg gac ctg ggc tac gag
       f   q   n   g   t   a   p   n   d   p   l   d   l   g   y   e
2497  gtg cag atc tgc agg tat aaa gac tac cga gag ccg ccg tgg tcg aa
       v   q   i   c   r   y   k   d   y   r   e   p   p   w   s   e
2545  aac aag tac gac atc tcc aag gac ttc tgg gcc gtc ctg gca gcc cgg
       n   k   y   d   i   s   k   d   f   w   a   v   l   a   a   r
2593  ctg gcg ttt gtc atc gtc ttc cag aac ctg gtc atg ttc atg agc gac
       l   a   f   v   i   v   f   q   n   l   v   m   f   m   s   d
2641  ttt gtg gac tgg gtc atc ccg gac atc ccc aag gac atc agc cag cag
       f   v   d   w   v   i   p   d   i   p   k   d   i   s   q   q
2689  atc cac aag gag aag gtg ctc atg gtg gag ctg ttc atg cgg gag gag
       i   h   k   e   k   v   l   m   v   e   l   f   m   r   e   e
2737  caa gac aag cag cag ctg ctg gaa acc tgg atg gag aag gag cgg cag
       q   d   k   q   q   l   l   e   t   w   m   e   k   e   r   q
2785  aag gac gag ccg ccg tgc aac cac cac aac acc aaa gcc tgc cca gac
       k   d   e   p   p   c   n   h   h   n   t   k   a   c   p   d
2833  agc ctc ggc agc cca gcc ccc agc cat gcc tac cac ggg ggc gtc ctg
       s   l   g   s   p   a   p   s   h   a   y   h   g   g   v   l
                             2881  tag
```

Figure 3 continued

B

```
  1  atg gtg agc aag ggc gag gag ctg ttc acc ggg gtg gtg ccc atc ctg
      m   v   s   k   g   e   e   l   f   t   g   v   v   p   i   l
 49  gtc gag ctg gac ggc gac gta aac ggc cac aag ttc agc gtg tcc ggc
      v   e   l   d   g   d   v   n   g   h   k   f   s   v   s   g
 97  gag ggc gag ggc gat gcc acc tac ggc aag ctg acc ctg aag ctg atc
      e   g   e   g   d   a   t   y   g   k   l   t   l   k   l   i
145  tgc acc acc ggc aag ctg ccc gtg ccc tgg ccc acc ctc gtg acc acc
      c   t   t   g   k   l   p   v   p   w   p   t   l   v   t   t
193  ttc ggc tac ggc ctg aag tgc ttc gcc cgc tac ccc gac cac atg aag
      f   g   y   g   l   k   c   f   a   r   y   p   d   h   m   k
241  cag cac gac ttc ttc aag tcc gcc atg ccc gaa ggc tac gtc cag gag
      q   h   d   f   f   k   s   a   m   p   e   g   y   v   q   e
289  cgc acc atc ttc ttc aag gac gac ggc aac tac aag acc cgc gcc gag
      r   t   i   f   f   k   d   d   g   n   y   k   t   r   a   e
337  gtg aag ttc gag ggc gac acc ctg gtg aac cgc atc gag ctg aag ggc
      v   k   f   e   g   d   t   l   v   n   r   i   e   l   k   g
385  atc gac ttc aag gag gac ggc aac atc ctg ggg cac aag ctg gag tac
      i   d   f   k   e   d   g   n   i   l   g   h   k   l   e   y
433  aac tac aac agc cag aac gtc tat ctg atg gcc gac aag cag aag aac
      n   y   n   s   q   n   v   y   l   m   a   d   k   q   k   n
481  ggc atc aag gtg aac ttc aag atc cgc cac aac atc gag gac ggc agc
      g   i   k   v   n   f   k   i   r   h   n   i   e   d   g   s
529  gtg cag ctc gcc gac cac tac cag cag aac acc ccc atc ggc gac ggc
      v   q   l   a   d   h   y   q   q   n   t   p   i   g   d   g
577  ccc gtg ctg ctg ccc gac aac cac tac ctg agc tac cag tcc gcc ctg
      p   v   l   l   p   d   n   h   y   l   s   y   q   s   a   l
625  agc aaa gac ccc aac gag aag cgc gat cac atg gtc ctg ctg gag ttc
      s   k   d   p   n   e   k   r   d   h   m   v   l   l   e   f
673  gtg acc gcc gcc ggg atc act ctc ggc atg gac gag ctg tac aag tga
      v   t   a   a   g   i   t   l   g   m   d   e   l   y   k   -
```

Figure 4 continued

Figure 10:
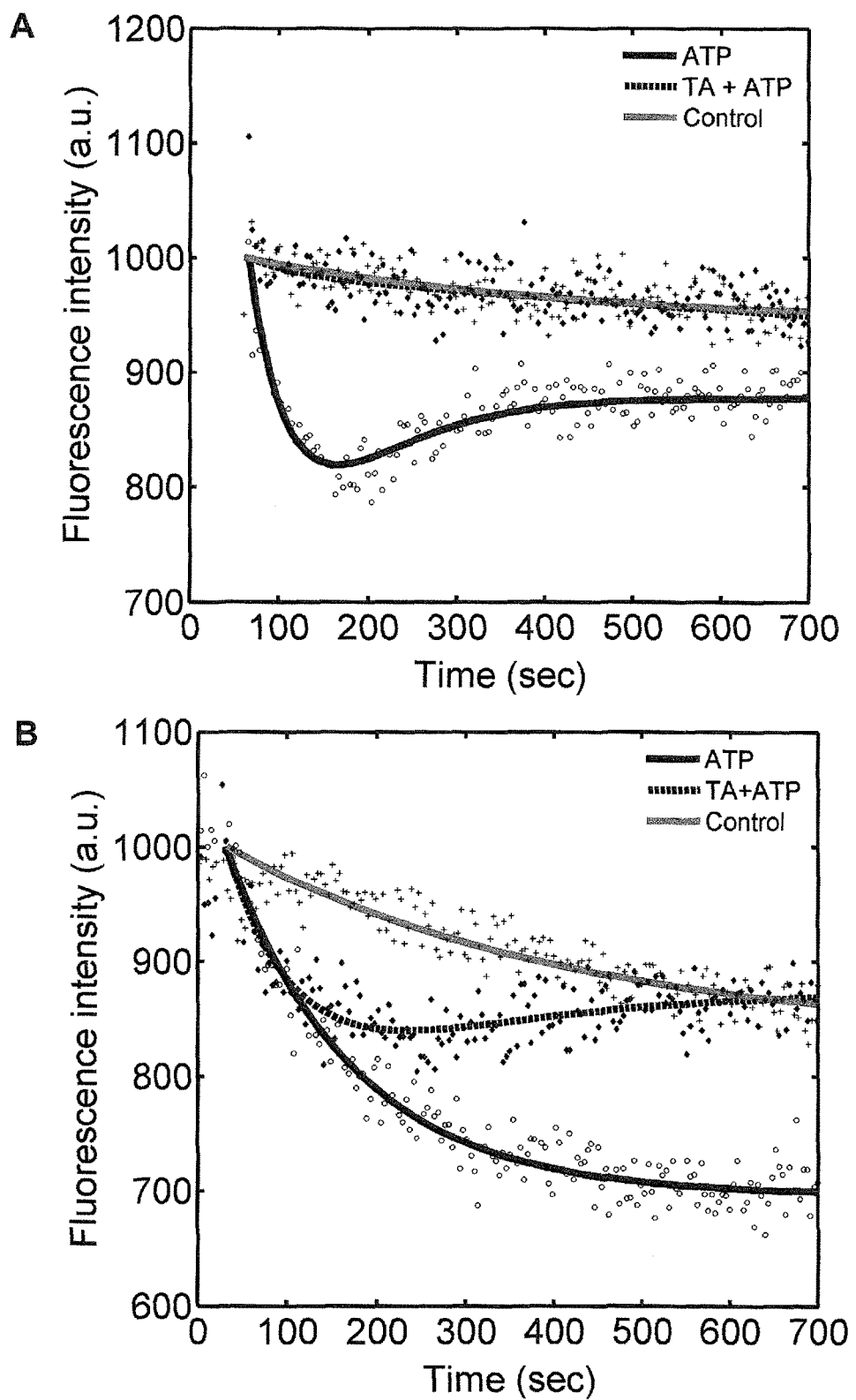

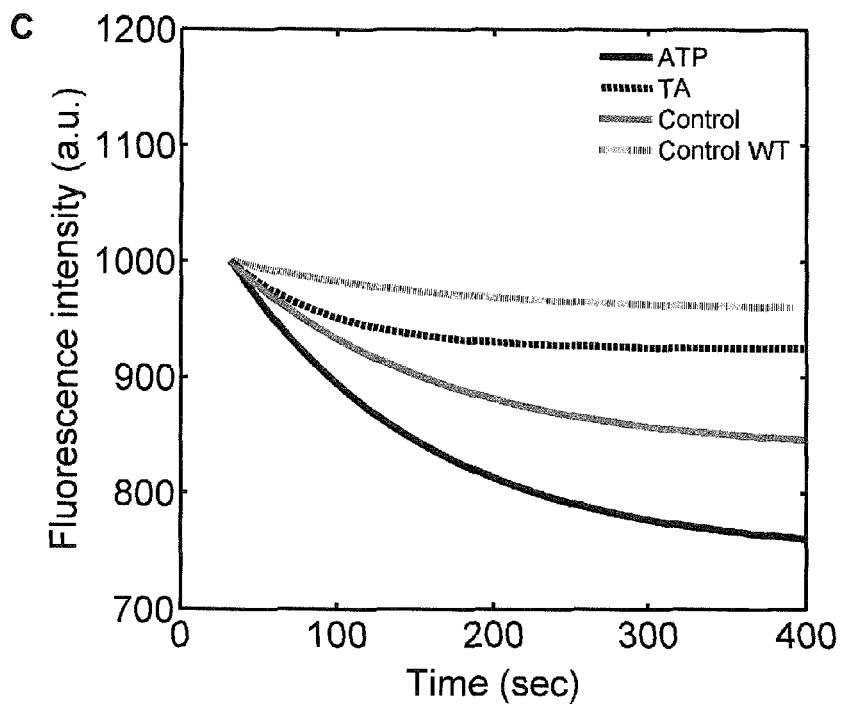
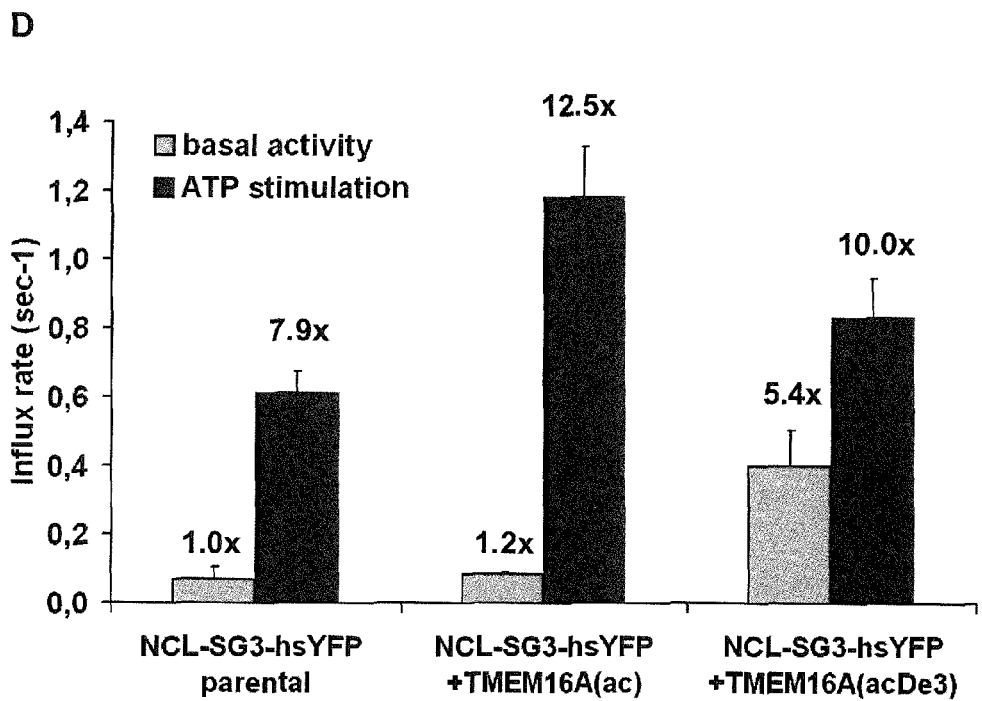
Figure 10 continued

CALCIUM-ACTIVATED CHLORIDE CHANNEL INVOLVED IN HUMAN SWEAT FORMATION

CROSS-REFERENCE TO RELATED APPLICATIONS

This application is the U.S. National Phase of International Patent Application No. PCT/EP2013/067044, filed Aug. 14, 2013, which claims the benefit of priority to European Patent Application No. 12180628.5, the contents of which are hereby incorporated by reference in their entireties.

The present invention relates to a nucleic acid molecule encoding a protein capable of forming a calcium-activated chloride channel, wherein said nucleic acid molecule comprises or consists of (a) a nucleic acid molecule encoding a protein having the amino acid sequence of SEQ ID NO:1; (b) a nucleic acid molecule having the DNA sequence of SEQ ID NO:2; (c) a nucleic acid molecule having the sequence of SEQ ID NO:2, wherein each thymine is replaced by uracil; (d) a nucleic acid molecule that hybridizes under stringent conditions to the complementary strand of a nucleic acid molecule of (a), (b) or (c); (e) a nucleic acid molecule encoding a protein having at least 97% sequence identity to the protein of (a); or (f) a nucleic acid molecule that is degenerate with respect to the nucleic acid molecule of (b), (c) or (d). The present invention further relates to a protein capable of forming a calcium-activated chloride channel, the use of the nucleic acid molecule of or the protein of the invention for identifying an inhibitor of sweat formation as well as an in vitro method of identifying an inhibitor of sweat formation.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Sweating is an important physiological process and has evolved in humans as a way to regulate body temperature. Human sweat formation occurs in eccrine sweat glands and can be divided in two functionally distinct steps: First, the secretory cells of the glands form an isotonic primary fluid by secretion of Cl$^-$ and Na$^+$ ions after nerval excitation. In a second step, part of the ions are reabsorbed by the connecting duct while the fluid is transported to the skin surface and hypotonic sweat is released through the pores (1). The main trigger of sweat formation is the release of cholinergic and adrenergic neurotransmitters such as acetylcholine and noradrenaline from the postganglionic, sympathetic nerve fibers that surround the secretory cells (1, 2). In addition, purinergic signals such as ATP or UTP are involved in the regulation of secretory activity of eccrine sweat glands (3-5).

Secretory cells respond to cholinergic and alpha-adrenergic stimulation by Ca$^{2+}$ uptake from the surrounding interstitium (1, 6, 7). In contrast, extracellular ATP or UTP activate purinergic receptors, which triggers the release of Ca$^{2+}$ from intracellular stores. In each case, the rise in cytoplasmic Ca$^{2+}$ concentrations subsequently stimulates Ca$^{2+}$-activated chloride channels (CaCCs), which drive the efflux of Cl$^-$ through the apical membrane into the sweat gland lumen (8). Ca$^{2+}$-activated chloride channels permit the passive ion transport along a Cl$^-$ gradient. Accordingly, the intracellular concentration of Cl$^-$ must be sufficiently high to form such a gradient. This is achieved by an electrically neutral co-transport of 2 Cl$^-$ with Na$^+$ and K$^+$ from the interstitium into the cell by Na—K-2Cl co-transporters and by the activities of Na—K-ATPase and K-channels to recycle K$^+$ (1, 9). Cl$^-$ efflux through Ca$^{2+}$-activated chloride channels results in an electrochemical gradient across the secretory epithelium (1, 10). In addition, the excess negative charges (Cl$^-$) drag Na$^+$ into the sweat gland lumen via an intercellular route, which leads to elevated luminal Cl$^-$ and Na$^+$ concentrations. The increase of luminal salt concentration establishes an osmotic gradient, which provides the driving force for the diffusion of water into the gland lumen forming isotonic primary sweat. Ca$^{2+}$-activated chloride channels can be considered as key-players in this process, as they mediate the trans-epithelial Cl— transport that initiates primary sweat formation.

Detailed biochemical and physiological characterization of sweat gland biology has so far been hampered by the absence of an in vivo sweat gland model system. An immortalized human sweat gland cell line, termed NCL-SG3, has been generated by Lee and Dessi (11) by infection of primary cells isolated from human eccrine sweat glands with simian virus 40 (SV40). Currently, this cell line represents the only available immortalized human sweat gland cell line.

NCL-SG3 cells retain important ultra-structural and physiological characteristics of native sweat gland epithelial cells. For instance, NCL-SG3 cells clearly show epithelial polarization with microvilli on the apical side as well as tight junctions and desmosomes to seal off the apical from the basolateral side, which ensures vectorial trans-epithelial ion transport (11, 12). Importantly, characteristic features of cells of the duct such as Na$^+$ re-absorption and expression of the Cl$^-$ channel cystic fibrosis transmembrane conductance regulator (CFTR) are apparently absent in NCL-SG3 cells (12-14), suggesting that the NCL-SG3 cells were derived from cells of the secretory coil of sweat glands and not from cells of the duct.

NCL-SG3 cells respond to natural agonists such as the beta-adrenergic activator isoproterenol and the purinergic activator ATP, much the same way as native sweat glands (11, 12, 14, 15). However, to cholinergic agents such as carbachol, NCL-SG3 cells only respond when they are grown on a permeable support (14, 15). Moreover, purinergic stimulation with ATP causes Cl$^-$ efflux in NCL-SG3 cells, which is dependent on the rise of the cytoplasmic Ca$^{2+}$ concentration, which is achieved by an initial Ca$^{2+}$ release from limited internal stores and is later sustained by Ca$^{2+}$ uptake. Importantly, treatment of NCL-SG3 cells with various Cl$^-$ channel inhibitors revealed that Cl$^-$ permeability is mediated by Ca$^{2+}$-activated Cl$^-$ channels. NCL-SG3 cells are therefore an appropriate model system to study Ca$^{2+}$-dependent Cl$^-$ secretion as the driving force for sweat formation in human eccrine sweat glands.

Although it has been known in the art that Ca$^{2+}$-activated chloride channels are required for trans-epithelial Cl$^-$ transport processes in sweat glands and other tissues, such as smooth muscle, airway and intestinal epithelia, the molecular identity of Ca$^{2+}$-activated chloride channels has remained elusive (8, 9, 16).

In today's modern society, extensive sweating is considered as unpleasant or even embarrassing and is mainly perceived as a cosmetic issue. Aluminium salts are often used for the treatment of hyperhidrosis at effective concentration that are much higher than in cosmetic antiperspirants (up to 10-30%) (17). Aluminium salts are also widely used in cosmetic formulations. However, the global use of aluminum salts as antiperspirants is much discussed because of controversial reports about potential health risks, such as contact allergies and breast cancer (18-21). The use of aluminum salts also raises cosmetic issues since they cause unsightly stains on clothing and large doses may damage clothing. In addition, the use of aluminium salts should be restricted to arm pits and is not recommended for use on palms and face. Common side effects include dermatitis and fissuring of the skin (17, 18). A more effective compound is Botulinum A toxin, which blocks the postganglionic, sympatathetic nerve fibres that stimulate sweating by inhibiting the release of the neurotransmitter acetylcholine. The treatment requires intradermal injections under anaesthetic by a physician. Side effects may include injection-site pain and flu-like symptoms (A.D.A.M. Medical Encyclopedia, U.S. National Library of Medicine). Another group of compounds, namely anti-cholinergic agents, are less often used since they target acetylcholine receptors, which are important for signal transduction in peripherial and central nervous system. Typcial side effects are blurred vision, micturition difficulties and dry mouth. In some cases, treatment of hyperhidrosis may even require complete excision of the sweating areas and removal of the subcutaneous tissue, which may lead to unsightly scares, poor wound healing and restriction of arm movements (17, 18).

Clearly, novel antiperspirants, which would directly target the initial step of sweat secretion mediated by calcium-activated chloride channels, have great potential to overcome the drawbacks and side effects of the above-mentioned approaches for treating excessive sweating. None of the compounds presently available in the art makes use of the potential to directly and specifically target this initial calcium-activated chloride channel-mediated step of sweat secretion. Instead, these presently employed compounds typically function via a physical obstruction of the sweat gland pore and channel.

Thus, despite the fact that a lot of effort has been invested into methods for identifying suitable antiperspirants, there is still a need to provide improved methods for the identification of novel antiperspirants that overcome the above described disadvantages.

This need is addressed by the provision of the embodiments characterized in the claims.

Accordingly, the present invention relates to a nucleic acid molecule encoding a protein capable of forming a calcium-activated chloride channel, wherein said nucleic acid molecule comprises or consists of (a) a nucleic acid molecule encoding a protein having the amino acid sequence of SEQ ID NO:1; (b) a nucleic acid molecule having the DNA sequence of SEQ ID NO:2; (c) a nucleic acid molecule having the sequence of SEQ ID NO:2, wherein each thymine is replaced by uracil; (d) a nucleic acid molecule that hybridizes under stringent conditions to the complementary strand of a nucleic acid molecule of (a), (b) or (c); (e) a nucleic acid molecule encoding a protein having at least 97% sequence identity to the protein of (a); or (f) a nucleic acid molecule that is degenerate with respect to the nucleic acid molecule of (b), (c) or (d).

Nucleic acid molecules, which are also referred to herein as polynucleotides, in accordance with the present invention, include DNA, such as cDNA or genomic DNA, and RNA. It is understood that the term "RNA" as used herein comprises all forms of RNA including mRNA, tRNA and rRNA. Preferably, embodiments reciting "RNA" are directed to mRNA. At the same time, other forms of RNA, including the above mentioned specific forms, are deliberately envisaged in the respective embodiments. Furthermore included is genomic RNA, such as in case of RNA of RNA viruses. Further included are nucleic acid mimicking molecules known in the art such as synthetic or semi-synthetic derivatives of DNA or RNA and mixed polymers, both sense and antisense strands. They may contain additional non-natural or derivatized nucleotide bases, as will be readily appreciated by those skilled in the art. In a preferred embodiment, the polynucleotide or the nucleic acid molecule(s) is/are DNA. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see, for example, Braasch and Corey, Chemistry & Biology 8, 1-7 (2001)). LNA is an RNA derivative in which the ribose ring is constrained by a methylene linkage between the 2'-oxygen and the 4'-carbon.

In those embodiments where the nucleic acid molecule comprises (rather than consists of) the recited sequence, additional nucleotides extend over the specific sequence either on the 5' end or the 3' end or both. Those additional nucleotides may be of heterologous or homologous nature. In the case of homologous sequences, these sequences may comprise up to 1500 nucleotides at the 5' and/or the 3' end, such as e.g. up to 1000 nucleotides, such as up to 900 nucleotides, more preferably up to 800 nucleotides, such as up to 700 nucleotides, such as e.g. up to 600 nucleotides, such as up to 500 nucleotides, even more preferably up to 400 nucleotides, such as up to 300 nucleotides, such as e.g. up to 200 nucleotides, such as up to 100 nucleotides, more preferably up to 50 nucleotides, such as up to 40 nucleotides such as e.g. up to 30 nucleotides, such as up to 20 nucleotides, more preferably up to 10 nucleotides and most preferably up to 5 nucleotides at the 5' and/or the 3' end. Furthermore, in the case of homologous sequences, those embodiments do not include complete genomes or complete chromosomes. Additional heterologous sequences may, for example, include heterologous promoters which are operatively linked to the coding sequences of the invention, as well as further regulatory nucleic acid sequences well known in the art and described in more detail herein below.

The term "up to [ . . . ] nucleotides", as used herein, relates to a number of nucleotides that includes any integer below and including the specifically recited number. For example, the term "up to 5 nucleotides" refers to any of 1, 2, 3, 4 and 5 nucleotides.

The term "protein", as used herein interchangeably with the term "polypeptide", describes linear molecular chains of amino acids, including single chain proteins or their fragments, containing more than 30 amino acids, whereas the term "peptide" as used herein describes a group of molecules consisting of up to 30 amino acids. Proteins, as well as peptides, may further form oligomers consisting of at least two identical or different molecules. The corresponding higher order structures of such multimers are, correspondingly, termed homo- or heterodimers, homo- or heterotrimers etc. Multimers giving rise or corresponding to the calcium-activated chloride channel of the present invention also fall under the definition of the term "protein". Furthermore, peptidomimetics of such proteins/peptides where amino acid(s) and/or peptide bond(s) have been replaced by functional analogues are also encompassed by the invention. Such functional analogues include all known amino acids other than the 20 gene-encoded amino acids, such as selenocysteine. The terms "protein" and "peptide" also refer to naturally modified proteins/peptides where the modification is effected e.g. by glycosylation, acetylation, phosphorylation and similar modifications which are well known in the art.

In accordance with the present invention, the nucleic acid molecule encodes "a protein capable of forming a calcium-activated chloride channel". Accordingly, it is required in accordance with the present invention that the protein is capable of forming a calcium-activated chloride channel. In accordance with one embodiment of the present invention, said protein has the amino acid sequence of SEQ ID NO:1, which represents a novel splice variant of the human TMEM16A calcium-activated chloride channel protein. The protein of SEQ ID NO:1 is for example encoded by a nucleic acid molecule having the DNA sequence of SEQ ID NO:2. Where the protein differs from the protein of SEQ ID NO:1 in accordance with the invention, it is required that said variant protein has the same or substantially the same biological function as the protein having the amino acid sequence of SEQ ID NO:1.

The biological function of the protein of SEQ ID NO:1 denotes in particular any known biological function of TMEM16A or any functions elucidated in accordance with the present invention. Non-limiting examples of said biological function are the activation by calcium and the subsequent chloride efflux from the cell.

These functions can be tested for by the skilled person either on the basis of common general knowledge or on the basis of the teachings of this specification, optionally in conjunction with the teachings of the documents cited therein. For example, methods based on electrophysiological technics can be employed, such as whole cell recordings, single channel recordings using intracellular implements with fine tipped microelectrodes, patch clamp microelectrodes with whole cells or with a membrane patch and incorporated ion channels into artificial lipid bilayers (22). Further techniques that can be employed are based on isotope efflux experiments, X-ray microanalysis, impedance measurements and fluorescent molecules to detect ions or measure the change of membrane potential. The methods can for example be applied to ion channels incorporated in artificial bilayers, purified ion channels, ion channels expressed in oocytes or in cell culture, as well as ion channels present in tissue or organs. Spectroscopic and crystallographic methods such as X-ray crystallography, electron microscopy, NMR and electron spin resonance or infra red spectroscopy can be applied as well to gain structural and functional information.

The term "hybridizes/hybridizing" as used herein refers to a pairing of a nucleic acid molecule to a (partially) complementary strand of this nucleic acid molecule which thereby form a double-stranded hybrid.

It is well known in the art how to perform hybridization experiments with nucleic acid molecules. Correspondingly, the person skilled in the art knows what hybridization conditions she/he has to use to allow for a successful hybridization in accordance with item (d), above. The establishment of suitable hybridization conditions is referred to in standard text books such as Sambrook and Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985).

"Stringent conditions" refers to hybridization conditions under which the nucleic acid molecules that are capable of hybridizing to the nucleic acid molecule of the invention or parts thereof do not cross hybridize to unrelated nucleic acid molecules. Stringent conditions are sequence-dependent and will be different in different circumstances. Appropriate stringent hybridization conditions for each nucleic acid sequence may be established by a person skilled in the art on well-known parameters such as temperature, composition of the nucleic acid molecules, salt conditions etc.; see, for example, Sambrook et al., "Molecular Cloning, A Laboratory Manual"; CSH Press, Cold Spring Harbor, 1989 or Higgins and Hames (eds.), loc. cit., see in particular the chapter "Hybridization Strategy" by Britten & Davidson, 3 to 15. Such conditions comprise, e.g. an overnight incubation at 65° C. in 4×SSC (600 mM NaCl, 60 mM sodium citrate) followed by washing at 65° C. in 0.1×SSC for one hour. Alternatively, hybridization conditions can comprise: an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulphate, and 20 µg/ml denatured, sheared salmon sperm DNA, followed by washing in e.g. 0.1-0.5×SSC at about 55-65° C. for about 5 to 20 min. Said conditions for hybridization are also known by a person skilled in the art as "highly stringent conditions for hybridization". Also contemplated are nucleic acid molecules that hybridize to the polynucleotides of the invention at lower stringency hybridization conditions ("low stringency conditions for hybridization"). Changes in the stringency of hybridization are primarily accomplished through the manipulation of formamide concentration (lower percentages of formamide result in lowered stringency), salt conditions, or temperature. For example, lower stringency conditions include an overnight incubation at 50° C. in 4×SSC or an overnight incubation at 37° C. in a solution comprising 6×SSPE (20×SSPE=3M NaCl; 0.2M NaH2PO4; 0.02M EDTA, pH 7.4), 0.5% SDS, 30% formamide, 100 mg/ml salmon sperm blocking DNA; followed by washes at 50° C. with 1×SSPE, 0.1% SDS. In addition, to achieve an even lower stringency, washes performed following stringent hybridization can be done at higher salt concentrations (e.g. 5×SSC). It is of note that variations in the above conditions may be accomplished through the inclusion and/or substitution of alternate blocking reagents. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The embodiment recited herein above preferably refers to highly stringent conditions and alternatively to conditions of lower stringency.

Also encompassed by the present invention are sequences that encode a protein that at least exhibits 97% identity with the above-recited protein. Preferably, the identity is at least 98%, more preferred at least 98.5%, more preferred at least 99%, even more preferred the identity is at least 99.5%, such as at least 99.8% and most preferably the identity is at least 99.9%. Such molecules may be homologous molecules from other species, such as orthologs, or mutated sequences from the same species to mention the most prominent examples.

In accordance with the present invention, the term "% sequence identity" describes the number of matches ("hits") of identical amino acids of two or more aligned amino acid sequences as compared to the number of amino acid residues making up the overall length of the amino acid sequences (or the overall compared part thereof). In other terms, using an alignment, for two or more sequences or sub-sequences the percentage of amino acid residues that are the same (e.g., 97% or 98% identity) may be determined, when the (sub) sequences are compared and aligned for maximum correspondence over a window of comparison, or over a designated region as measured using a sequence comparison algorithm as known in the art, or when manually aligned and visually inspected. Preferred proteins in accordance with the invention are those where the described identity exists over a region that is at least about 15 to 25 amino acids in length, more preferably, over a region that is at least about 50 to 100 amino acids in length. More preferred proteins in accordance with the present invention are those having the described sequence identity over the entire length of the protein of (a).

Methods to evaluate the identity level between two molecules are well known in the art. For example, the sequences can be aligned electronically using suitable computer programs known in the art. Such programs comprise BLAST (Altschul et al. (1990) J. Mol. Biol. 215, 403), variants thereof such as WU-BLAST (Altschul and Gish (1996) Methods Enzymol. 266, 460), FASTA (Pearson and Lipman (1988) Proc. Natl. Acad. Sci. USA 85, 2444) or implementations of the Smith-Waterman algorithm (SSEARCH, Smith and Waterman (1981) J. Mol. Biol., 147, 195). These programs, in addition to providing a pairwise sequence alignment, also report the sequence identity level (usually in percent identity) and the probability for the occurrence of the alignment by chance (P-value).

The NCBI BLAST algorithm is preferably employed in accordance with this invention. The BLASTP program for amino acid sequences uses as default a word length (W) of 3, and an expectation (E) of 10. The BLOSUM62 scoring matrix (Henikoff, Proc. Natl. Acad. Sci., 1989, 89:10915) uses alignments (B) of 50, expectation (E) of 10, M=5, N=4, and a comparison of both strands. Accordingly, all the nucleic acid molecules having the prescribed function and further having a sequence identity of at least 97% as determined with the NCBI BLAST programme fall under the scope of the invention.

It will be appreciated that the protein having at least 97% sequence identity to the protein of (a) has to fulfil the requirement of being a protein capable of forming a calcium-activated chloride channel. Preferably, the protein retains or essentially retains the biological activity of the protein of SEQ ID NO:1.

In accordance with the present invention, the biological activity of the protein of SEQ ID NO:1 is essentially retained if at least 60% of the biological activity of the protein of SEQ ID NO:1 is retained. Preferably, at least 75% or more preferably at least 80% of the activity of the protein of SEQ ID NO:1 is retained. More preferred is that at least 90% such as at least 95%, even more preferred at least 98% such as at least 99% of the biological activity of the protein of SEQ ID NO:1 is retained. Most preferred is that the biological activity is fully, i.e. to 100%, retained. Also in accordance with the invention are polypeptides having an increased biological activity compared to the protein of SEQ ID NO:1, i.e. more than 100% activity. Preferably, the biological activity employed for comparison with the protein of SEQ ID NO:1 is the activation by calcium and the subsequent chloride efflux from the cell, either of which or both together may be analysed for this comparison.

It will be understood by the person skilled in the art that the biological activity of the protein of SEQ ID NO:1 refers to the function defined herein above. Methods of assessing the biological activity of the protein of the invention have been discussed herein above.

The term "degenerate" in accordance with the present invention refers to the redundancy of the genetic code. Degeneracy results because there are more codons than encodable amino acids. For example, if there were two bases per codon, then only 16 amino acids could be coded for ($4^2$=16). Because at least 21 codes are required (20 amino acids plus stop), and the next largest number of bases is three, then $4^3$ gives 64 possible codons, meaning that some degeneracy must exist. As a result, some amino acids are encoded by more than one triplet, i.e. by up to six triplets. The degeneracy mostly arises from alterations in the third position in a triplet. This means that nucleic acid molecules having a different sequence than the nucleic acid sequence specified above, but still encoding the same polypeptide, lie within the scope of the present invention. Such nucleic acid molecules are referred to herein as being degenerate with respect to another nucleic acid molecule.

In accordance with the present invention, a novel calcium-dependent chloride channel protein was identified that is involved in human sweat formation. This novel protein is a so-far unknown splice variant of TMEM16A. TMEM16A was recently identified as a CaCC (23-25) and was shown to be expressed in a variety of different cell types and tissues (26). Strikingly, despite its high abundance in airway and intestinal cells, TMEM16A was shown to be only a minor functional component in these cell types and it was suggested that cr secretion may depend on other, not yet identified CaCCs (27). In accordance with the present invention it was surprisingly found that TMEM16A is not only expressed in secretory sweat gland cells and whole eccrine sweat glands, but is the major functional component in secretory sweat gland cells which indicates a major role of TMEM16A in sweat formation.

Due to alternative splicing, multiple TMEM16A protein isoforms with different functional properties have been described (23, 26). Interestingly, each cell type and tissue expresses a characteristic set of various TMEM16A isoforms rather than a single tissue-specific splice variant (26). A lot of effort has been invested in the identification of alternatively spliced exons and the characterization of the resulting TMEM16A isoforms (23, 26, 28). So far, four alternatively spliced protein segments (termed a, b, c and d, encoded by exon-1, 6b, 13 and 15, respectively) have been identified and were shown to influence the function of TMEM16A (23, 26, 29). Despite extensive efforts that have already been made, an additional, alternatively spliced exon (exon-3), was surprisingly discovered in accordance with the present invention, which codes for protein segment e3 of TMEM16A in sweat gland cells. Most importantly, the corresponding novel TMEM16A isoform (termed TMEM16A(acΔe3) herein), which lacks the protein segment e3, is characterized by different functional properties as compared to the known TMEM16A isoforms. The identification of this novel isoform present in sweat glands highlights the unique composition of TMEM16A isoforms, which generate highly specific Cl⁻ currents to meet the exact needs of the cells they are expressed in. The here discovered TMEM16A(acΔe3) splice variant finds numerous applications. For example, it can be used as a novel screening target, which for the first time permits the identification of highly specific inhibitors of sweat secretion. Such highly specific inhibitors have great potential to improve existing cosmetic antiperspirant formulations and pharmaceuticals used in the treatment of excessive sweating (hyperhidrosis).

The present invention further relates to a vector comprising the nucleic acid molecule of the invention.

Preferably, the vector is a plasmid, cosmid, virus, bacteriophage or another vector used conventionally e.g. in genetic engineering.

The nucleic acid molecule of the present invention may be inserted into several commercially available vectors. Non-limiting examples include prokaryotic plasmid vectors, such as pQE-12,the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORTI (GIBCO BRL), pGEMHE (Promega), pLXIN, pSIR (Clontech), pIRES-EGFP (Clontech), pEAK-10 (Edge Biosystems) pTriEx-Hygro (Novagen) and pCl-Neo (Promega). Examples for plasmid vectors suitable for *Pichia pastoris* comprise e.g. the plasmids pAO815, pPIC9K and pPIC3.5K (all Invitrogen). Another vector suitable for expressing proteins in *Xenopus* embryos, zebrafish embryos as well as a wide variety of mammalian and avian cells is the multipurpose expression vector pCS2+.

The nucleic acid molecule of the present invention referred to above may also be inserted into vectors such that a translational fusion with another nucleic acid molecule is generated. The other nucleic acid molecules may e.g. encode a protein that increases the solubility and/or facilitates the purification of the binding molecule encoded by the nucleic acid molecule of the invention or a protein of interest that is to be observed by fluorescence imaging. Non-limiting examples of such vectors include pET32, pET41, pET43. The vectors may also contain an additional expressible polynucleotide coding for one or more chaperones to facilitate correct protein folding. Suitable bacterial expression hosts comprise e. g. strains derived from TG1, BL21 (such as BL21(DE3), BL21(DE3)PlysS, BL21(DE3)RIL, BL21(DE3)PRARE) or Rosettaâ.

For vector modification techniques, see Sambrook and Russel, loc.cit. Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Such regulatory sequences are well known to those skilled in the art and include, without being limiting, regulatory sequences ensuring the initiation of transcription, internal ribosomal entry sites (IRES) (Owens, Proc. Natl. Acad. Sci. USA 98 (2001), 1471-1476) and optionally regulatory elements ensuring termination of transcription and stabilization of the transcript. Non-limiting examples for regulatory elements ensuring the initiation of transcription comprise a translation initiation codon, enhancers such as e.g. the SV40-enhancer, insulators and/or promoters, such as for example the cytomegalovirus (CMV) promoter, SV40-promoter, RSV-promoter (Rous sarcome virus), the lacZ promoter, chicken beta-actin promoter, CAG-promoter (a combination of chicken beta-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the lacUV5 promoter, the autographa californica multiple nuclear polyhedrosis virus (AcMNPV) polyhedral promoter or a globin intron in mammalian and other animal cells. The lac promoter is a typical inducible promoter, useful for prokaryotic cells, which can be induced using the lactose analogue isopropylthiol-b-D-galactoside ("IPTG"). Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence of the invention. Additional regulatory elements may include translational enhancers, Kozak sequences and intervening sequences flanked by donor and acceptor sites for RNA splicing, nucleotide sequences encoding secretion signals or, depending on the expression system used, signal sequences capable of directing the expressed protein to a cellular compartment. For example an N-terminal flanking sequence or "leader sequence", which is also referred to as "signal peptide" in the art, may be included. The skilled person can choose suitable leader sequences without further ado. A leader sequence is preferably employed to ensure the correct localization of a protein but is no longer required in the expressed, mature protein. Moreover, elements such as origin of replication, drug resistance gene, regulators (as part of an inducible promoter) may also be included.

An expression vector according to this invention is capable of directing the replication, and the expression of the nucleic acid molecule of the invention and the calcium-activated chloride channel encoded thereby.

The co-transfection with a selectable marker such as dhfr, gpt, neomycin, hygromycin, blasticidin or geneticin, allows the identification and isolation of the transfected cells. The transfected nucleic acid molecules can also be amplified to express large amounts of the encoded molecule. The DHFR (dihydrofolate reductase) marker is useful to develop cell lines that carry several hundred or even several thousand copies of the gene of interest. Another useful selection marker is the enzyme glutamine synthase (GS). Using these markers, the cells are grown in selective medium and the cells with the highest resistance are selected. Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The nucleic acid molecules of the invention as described herein above may be designed for introduction into cells by e.g. chemical based methods (calcium phosphate, liposomes, DEAE-dextrane, polyethylenimine, nucleofection), non chemical methods (electroporation, sonoporation, optical transfection, gene electrotransfer, hydrodynamic delivery or naturally occurring transformation upon contacting cells with the nucleic acid molecule of the invention), particle-based methods (gene gun, magnetofection, impalefection) phage vector-based methods and viral methods (e.g. adenoviral, retroviral, lentiviral methods). Additionally, baculoviral systems or systems based on Vaccinia Virus or Semliki Forest Virus can also be used as vector in eukaryotic expression system for the nucleic acid molecules of the invention. Expression vectors derived from viruses such as retroviruses, vaccinia virus, adeno-associated virus, herpes viruses, or bovine papilloma virus, may be used for delivery of the nucleic acid molecules or vector into targeted cell population. Methods which are well known to those skilled in the art can be used to construct recombinant viral vectors; see, for example, the techniques described in Sambrook and Russel "Molecular Cloning, A Laboratory Manual", Cold Spring Harbor Laboratory, N.Y. (2001) and Ausubel et al., Current Protocols in Molecular Biology, Green Publishing Associates and Wiley Interscience, N.Y. (2001). Where the nucleic acid molecules are to be introduced into the nucleus, preferred methods are e.g. microinjection or nucleofection. Methods for carrying out microinjection are well known in the art and are described for example in Nagy et al. (Nagy A, Gertsenstein M, Vintersten K, Behringer R., 2003. Manipulating the Mouse Embryo. Cold Spring Harbour, N.Y.: Cold Spring Harbour Laboratory Press).

The present invention further relates to a host cell or a non-human host transformed with the vector of the invention.

Suitable prokaryotic hosts comprise e.g. bacteria of the species *Escherichia, Streptomyces, Salmonella* or *Bacillus*. Suitable eukaryotic host cells are e.g. yeasts such as *Saccharomyces cerevisiae, Pichia pastoris, Schizosaccharomyces pombe* or chicken cells, such as e.g. DT40 cells. Insect cells suitable for expression are e.g. *Drosophila* S2, *Drosophila* Kc, or *Spodoptera* Sf9 and Sf21 cells. Suitable zebrafish cell lines include, without being limiting, ZFL, SJD or ZF4.

Mammalian host cells that could be used include, human Hela, HEK293, H9 and Jurkat cells, mouse NIH3T3 and C127 cells, COS 1, COS 7 and CV1, quail QC1-3 cells, mouse L cells, mouse sarcoma cells, Bowes melanoma cells and Chinese hamster ovary (CHO) cells. Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells), human dermal and pulmonary fibroblasts, human epithelial cells (nasal, tracheal, renal, placental, intestinal, bronchial epithelial cells), human secretory cells (from salivary, sebaceous and sweat glands), human endocrine cells (thyroid cells), human adipose cells, human smooth muscle cells, human skeletal muscle cells, and stable, immortalized cell lines derived thereof (for example hTERT or oncogene immortalized cells).

Appropriate culture media and conditions for the above described host cells are known in the art.

Transgenic non-human animals as hosts transfected with and/or expressing the nucleic acid molecule of the present invention also lie within the scope of the invention. In a preferred embodiment, the transgenic animal is a fish, such as e.g. zebrafish or a mammal, e.g. a mouse, rat, hamster, cow, cat, pig, dog, horse, rabbit or monkey.

Methods for the production of a transgenic non-human animal include for example methods for the production of transgenic mice or other mammals, which usually comprise introduction of the nucleic acid molecule or targeting vector of the present invention into a germ cell, an embryonic cell, stem cell or an egg or a cell derived therefrom. Production of transgenic embryos and screening of those can be performed, e.g., as described by A. L. Joyner Ed., Gene Targeting, A Practical Approach (1993), Oxford University Press. The DNA of the embryonic membranes of embryos can be analyzed using, e.g., Southern blots with an appropriate probe. A general method for making transgenic non-human animals is described in the art; see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326:292-295 (1987)), the D3 line (Doetschman et al., J. Embryol. Exp. Morph. 87:27-45 (1985)), the CCE line (Robertson et al., Nature 323:445-448 (1986)), the AK-7 line (Zhuang et al., Cell 77:875-884 (1994)). The success of generating a mouse line from ES cells bearing a specific targeted mutation depends on the pluripotency of the ES cells (i. e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant non-human females and are born, e.g. as chimeric mice. The resultant chimeric transgenic mice are backcrossed and screened for the presence of the correctly targeted transgene(s) by PCR or Southern blot analysis on tail biopsy DNA of offspring so as to identify heterozygous transgenic mice.

The host cell or cells obtained from the non-human animal in accordance with this embodiment may for example be employed in methods for the identification of inhibitors of sweat formation, as described in more detail herein below.

Furthermore, the present invention also relates to a method of producing a protein capable of forming a calcium-activated chloride channel comprising culture of the host cell of the present invention under suitable conditions and isolation of the calcium-activated chloride channel molecule produced. Preferably, the method is carried out using host cells, such as e.g. bacterial cells.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be over-expressed. In general, the skilled person is also aware that these conditions may have to be adapted to the needs of the host and the requirements of the protein expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g. be carried out in RPMI, Williams' E or DMEM medium containing 10% (v/v) FCS, 2 mM L-glutamine and 100 U/ml penicillin/streptomycine. The cells can be kept e.g. at 37° C. or at 41° C. for DT40 chicken cells, in a 5% $CO_2$, water saturated atmosphere. Suitable media for insect cell culture is e.g. TNM+10% FCS or SF900 medium. Insect cells are usually grown at 27° C. as adhesion or suspension culture. Suitable expression protocols for eukaryotic or vertebrate cells are well known to the skilled person and can be retrieved e.g. from Sambrook and Russel, loc.cit.

Methods of isolation of the protein produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook and Russel, loc.cit.

It will be appreciated by the skilled person that the term "isolation of the calcium-activated chloride channel molecule produced" refers to the isolation of the protein encoded by the nucleic acid molecule of the present invention.

The present invention further relates to a protein capable of forming a calcium-activated chloride channel encoded by the nucleic acid molecule of the invention or produced by the method of the invention.

The protein of the present invention may be generated by molecular cloning techniques, for example recombinant expression can be accomplished using expression vectors and hosts as described above.

Furthermore, the protein of the present invention can also be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. Chemical synthesis also includes the solid phase procedure described by Houghton (Proc. Natl. Acad. Sci., 1985, 82: 5131). Furthermore, the protein of the invention may be produced semi-synthetically, for example by a combination of recombinant and synthetic production.

The present invention also relates to the use of the nucleic acid molecule, the vector, the host or host cell or the protein of the invention for identifying an inhibitor of sweat formation.

As described herein above, sweating is an important physiological process. However, extensive sweating is considered as unpleasant or even embarrassing and the identification of inhibitors of sweat formation therefore remains an important research goal for therapeutic as well as cosmetic uses. Due to the identification of the novel calcium-activated chloride channel of the present invention, and the elucidation of its pivotal role in calcium-activated chloride transport in secretory sweat gland cells, it is now possible to employ this protein or the nucleic acid molecule encoding same as well as vectors and hosts/host cells comprising same in screening methods for identifying compounds that inhibit this proteins activity, thereby reducing or inhibiting sweat formation. To this end, the effect of a potential inhibitor of the calcium-activated chloride channel of the invention may be tested e.g. in intact cells expressing the protein of the present invention, such as for example described herein below, or for example by using artificial membrane systems. Such systems include liposomes, artificial bilayers of phospholipids, isolated plasma membrane such as cell membrane fragments, cell membrane fractions, or cell membrane vesicles. The protein of the invention may be incorporated into such an artificial membrane system and the activation of the calcium-activated chloride channel of the invention in the absence and the presence of the candidate inhibitor can be compared, using appropriate means to detect the activation of the channel (e.g., chloride flux from one side of the membrane system to the other side). Other test systems may be based on in vitro binding and interaction studies. Such assays make use of a purified protein of interest and purified test components. The binding or interaction of the purified calcium-activated chloride channel of the invention in the absence and the presence of the candidate inhibitor can be compared, using appropriate means to detect the binding of the candidate inhibitor to the channel, including, without being limiting, fluorescently labelled inhibitors or a fluorescently labelled protein of the invention.

The term "inhibitor", according to the present invention, relates to a compound lowering the activity of a target molecule, i.e. in the present case the calcium-activated chloride channel of the invention, preferably by performing one or more of the following effects: (i) the transcription of the gene encoding the protein to be inhibited is lowered, (ii) the translation of the mRNA encoding the protein to be inhibited is lowered, (iii) the protein performs its biochemical function with lowered or abolished efficiency in the presence of the inhibitor, and (iv) the protein performs its cellular function with lowered or abolished efficiency in presence of the inhibitor.

Compounds falling in class (i) include compounds interfering with the transcriptional machinery and/or its interaction with the promoter of said gene and/or with expression control elements remote from the promoter such as enhancers. Compounds of class (ii) comprise antisense constructs and constructs for performing RNA interference (e.g. siRNA, shRNA, miRNA) well known in the art (see, e.g. Zamore (2001) Nat. Struct. Biol. 8(9), 746; Tuschl (2001) Chembiochem. 2(4), 239). Compounds of class (iii) interfere with the molecular function of the protein to be inhibited, in the present case with the ability of the calcium-activated chloride channel of the invention to permit the transport of chloride across the membrane and the accompanying fluid secretion. Accordingly, compounds blocking the ion channel pore, in particular compounds capable of causing conformational changes of the ion channel, interefering with ion channel dimerization, competing with regulatory proteins or calcium binding site, prolonging or shortening the closed state or the open state of the ion channel are envisaged. Class (iv) includes compounds which do not necessarily bind directly to the calcium-activated chloride channel of the invention, but still interfere with its activity, for example by binding to and/or inhibiting the function or expression of members of the pathway which comprises said protein. These members may be either upstream or downstream of the calcium-activated chloride channel of the invention within said pathway. As non-limiting examples, activation of the calcium-activated chloride channel by reducing the availability of calcium may be inhibited.

In a preferred embodiment, the remaining level of activity after inhibition is less than 90%, more preferred less than 80%, less than 70%, less than 60% or less than 50% of the activity of the calcium-activated chloride channel of the invention in the absence of the inhibitor. Yet more preferred are inhibitors lowering the level to less than 25%, less than 10%, less than 5% or less than 1% of the activity of the calcium-activated chloride channel of the invention in the absence of the inhibitor. Preferably, the inhibitor results in an inhibition of sweat formation of a subject, such as e.g. a human subject, by at least 10%, more preferably at least 20%, at least 30%, at least 40% and even more preferably at least 50%, such as e.g. at least 60%, at least 70%, at least 80% and yet more preferably at least 90%. Most preferably, the inhibitor results in a total inhibition of sweat formation in a subject.

The efficiency of the potential inhibitor can be quantified by comparing the level of activity of the calcium-activated chloride channel of the invention in the presence of the inhibitor to the activity of said channel in the absence of the inhibitor. For example, as an activity measure may be used: the change in amount of mRNA formed, the change in amount of protein formed, the change in amount of chloride transport across the channel or the change in amount of fluid secretion, and/or the change in the cellular phenotype or in the phenotype of an organism.

Means and methods to determine these changes are well known in the art. The determination of binding of potential inhibitors can be effected in, for example, any binding assay, preferably biophysical binding assay, which may be used to identify binding test molecules prior to performing the functional/activity assay with the inhibitor. Suitable biophysical binding assays are known in the art and comprise fluorescence polarisation (FP) assay, fluorescence resonance energy transfer (FRET) assay and surface plasmon resonance (SPR) assay.

In cases where the inhibitor acts by affecting the expression level of the target protein, the determination of the expression level of the protein can, for example, be carried out on the nucleic acid level or on the amino acid level. Methods for determining the expression of a protein on the nucleic acid level include, but are not limited to, northern blotting, PCR, RT-PCR or real time RT-PCR. These methods are well known in the art. Methods for the determination of the expression of a protein on the amino acid level include but are not limited to western blotting or polyacrylamide gel electrophoresis in conjunction with protein staining techniques such as Coomassie Brilliant blue or silver-staining. Also of use in protein quantification is the Agilent Bioanalyzer technique.

In the case where an inhibitor affects the amounts of chloride transport across the channel or the change in amount of fluid secretion, determination of said effect may be accomplished by methods based on electrophysiological techniques, such as whole cell or single channel recordings (voltage and patch clamp techniques), isotope efflux experiments, X-ray microanalysis or fluorescent ion binding molecules as well as the methods shown in the appended examples.

The function of an inhibitor may be identified and/or verified by using high throughput screening assays (HTS). High-throughput assays, independently of being biochemical, cellular or other assays, generally may be performed in wells of microtiter plates, wherein each plate may contain, for example 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to the observed biological activity.

In a preferred embodiment of the use of the invention, the inhibitor is a small molecule, an antibody, an aptamer/spiegelmer, an siRNA, an shRNA, an miRNA, a ribozyme or an antisense nucleic acid molecule.

A "small molecule" according to the present invention may be, for example, an organic molecule. Organic molecules relate or belong to the class of chemical compounds having a carbon basis, the carbon atoms linked together by carbon-carbon bonds. The original definition of the term organic related to the source of chemical compounds, with organic compounds being those carbon-containing compounds obtained from plant or animal or microbial sources, whereas inorganic compounds were obtained from mineral sources. Organic compounds can be natural or synthetic. Alternatively, the "small molecule" in accordance with the present invention may be an inorganic compound. Inorganic compounds are derived from mineral sources and include all compounds without carbon atoms (except carbon dioxide, carbon monoxide and carbonates). Preferably, the small molecule has a molecular weight of less than about 2000 amu, or less than about 1000 amu such as less than about 500 amu, and even more preferably less than about 250 amu. The size of a small molecule can be determined by methods well-known in the art, e.g., mass spectrometry. The small molecules may be designed, for example, based on the crystal structure of the target molecule, where sites presumably responsible for the biological activity, can be identified and verified in in vivo assays such as in vivo high-throughput screening (HTS) assays. Such small molecules may be particularly suitable as inhibitors by blocking specific bindings sites of the target molecule.

The term "antibody" as used in accordance with the present invention comprises polyclonal and monoclonal antibodies, as well as derivatives or fragments thereof, which still retain binding specificity. Antibody fragments or derivatives comprise, inter alia, Fab or Fab' fragments as well as Fd, F(ab')$_2$, Fv or scFv fragments; see for example Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also includes embodiments such as chimeric (human constant domain, non-human variable domain), single chain and humanized (human antibody with the exception of non-human CDRs) antibodies.

Various techniques for the production of antibodies are well known in the art and described, e.g. in Harlow and Lane (1988) and (1999), loc. cit. In addition, the antibodies can be produced as peptidomimetics. Further, techniques described for the production of single chain antibodies (see, inter alia, U.S. Pat. No. 4,946,778) can be adapted to produce single chain antibodies specific for the target of this invention. Also, transgenic animals or plants (see, e.g., U.S. Pat. No. 6,080,560) may be used to express (humanized) antibodies specific for the target of this invention. Most preferably, the antibody is a monoclonal antibody, such as a human or humanized antibody. For the preparation of monoclonal antibodies, any technique which provides antibodies produced by continuous cell line cultures can be used. Examples for such techniques are described, e.g. in Harlow and Lane (1988) and (1999), loc. cit. and include the hybridoma technique originally developed by Köhler and Milstein Nature 256 (1975), 495-497, the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of the target protein (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, inter alia, viruses or plasmid vectors.

Aptamers are nucleic acid or peptide molecules that bind a specific target molecule. More specifically, aptamers can be classified as nucleic acid aptamers, such as DNA or RNA aptamers, or peptide aptamers. Whereas the former normally consist of (usually short) strands of oligonucleotides, the latter preferably consist of a short variable peptide domain, attached at both ends to a protein scaffold. Whereas nucleic acid aptamers are nucleic acid molecules that are in the natural D-conformation, the corresponding nucleic acid molecules that are in the L-conformation are referred to in the art and herein as spiegelmers.

Aptamers, as well as spiegelmers, are usually created by selecting them from a large random sequence pool, but natural aptamers also exist in riboswitches. Aptamers and spiegelmers can be used as macromolecular drugs. They can be combined with ribozymes to self-cleave in the presence of their target molecule. These compound molecules have additional research, industrial and clinical applications (Osborne et. al. (1997), Current Opinion in Chemical Biology, 1:5-9; Stull & Szoka (1995), Pharmaceutical Research, 12, 4:465-483).

In accordance with the present invention, the term "small interfering RNA (siRNA)", also known as short interfering RNA or silencing RNA, refers to a class of 18 to 30, preferably 19 to 25, most preferred 21 to 23 or even more preferably 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

siRNAs naturally found in nature have a well defined structure: a short double-strand of RNA (dsRNA) with 2-nt 3' overhangs on either end. Each strand has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Essentially any gene of which the sequence is known can thus be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Exogenously introduced siRNAs may be devoid of overhangs at their 3' and 5' ends, however, it is preferred that at least one RNA strand has a 5'- and/or 3'-overhang. Preferably, one end of the double-strand has a 3'-overhang from 1-5 nucleotides, more preferably from 1-3 nucleotides and most preferably 2 nucleotides. The other end may be blunt-ended or has up to 6 nucleotides 3'-overhang. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3' overhangs on either end. The sequence of the 2-nt 3' overhang makes a small contribution to the specificity of target recognition restricted to the unpaired nucleotide adjacent to the first base pair (Elbashir et al. 2001). 2'-deoxynucleotides in the 3' overhangs are as efficient as ribonucleotides, but are often cheaper to synthesize and probably more nuclease resistant. Delivery of siRNA may be accomplished using any of the methods known in the art, for example by combining the siRNA with saline and administering the combination intravenously or intranasally or by formulating siRNA in glucose (such as for example 5% glucose) or cationic lipids and polymers can be used for siRNA delivery in vivo through systemic routes either intravenously (IV) or intraperitoneally (IP) (Fougerolles et al. (2008), Current Opinion in Pharmacology, 8:280-285; Lu et al. (2008), Methods in Molecular Biology, vol. 437: Drug Delivery Systems—Chapter 3: Delivering Small Interfering RNA for Novel Therapeutics).

A short hairpin RNA (shRNA) is a sequence of RNA that makes a tight hairpin turn that can be used to typically silence gene expression via RNA interference. shRNA can for example use a vector introduced into cells, in which case preferably the U6 promoter is utilized to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

Preferably, si/shRNAs to be used in the present invention are chemically synthesized using conventional methods that, for example, appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs or shRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

Further molecules effecting RNAi include, for example, microRNAs (mIRNA). Said RNA species are single-stranded RNA molecules which, as endogenous RNA molecules, regulate gene expression. Binding to a complementary mRNA transcript triggers the degradation of said mRNA transcript through a process similar to RNA interference. Accordingly, mIRNA may be employed as an inhibitor of the calcium-activated chloride channel of the present invention.

A ribozyme (from ribonucleic acid enzyme, also called RNA enzyme or catalytic RNA) is an RNA molecule that catalyzes a chemical reaction. Many natural ribozymes catalyze either their own cleavage or the cleavage of other RNAs, but they have also been found to catalyze the aminotransferase activity of the ribosome. Non-limiting examples of well-characterized small self-cleaving RNAs are the hammerhead, hairpin, hepatitis delta virus, and in vitro-selected lead-dependent ribozymes, whereas the group I intron is an example for larger ribozymes. The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site. The basic principle of constructing hammerhead ribozymes is as follows: An interesting region of the RNA, which contains the GUC (or CUC) triplet, is selected. Two oligonucleotide strands, each usually with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences.

A recent development, also useful in accordance with the present invention, is the combination of an aptamer recognizing a small compound with a hammerhead ribozyme. The conformational change induced in the aptamer upon binding the target molecule is supposed to regulate the catalytic function of the ribozyme.

The term "antisense nucleic acid molecule" is well known in the art and refers to a nucleic acid which is complementary to a target nucleic acid, i.e. a nucleic acid encoding the target protein. An antisense molecule in accordance with the invention is capable of interacting with the target nucleic acid, more specifically it is capable of hybridizing with the target nucleic acid. Due to the formation of the hybrid, transcription of the target gene(s) and/or translation of the target mRNA is reduced or blocked. Standard methods relating to antisense technology have been described (see, e.g., Melani et al., Cancer Res. (1991) 51:2897-2901).

Also encompassed herein are modified versions of these inhibitory compounds.

The term "modified versions of these inhibitory compounds" in accordance with the present invention refers to versions of the compounds that are modified to achieve i) modified spectrum of activity, organ specificity, and/or ii) improved potency, and/or iii) decreased toxicity (improved therapeutic index), and/or iv) decreased side effects, and/or v) modified onset of therapeutic action, duration of effect, and/or vi) modified pharmacokinetic parameters (resorption, distribution, metabolism and excretion), and/or vii) modified physico-chemical parameters (solubility, hygroscopicity, color, taste, odor, stability, state), and/or viii) improved general specificity, organ/tissue specificity, and/or ix) optimised application form and route by, for example, (a) esterification of carboxyl groups, or (b) esterification of hydroxyl groups with carboxylic acids, or (c) esterification of hydroxyl groups to, e.g. phosphates, pyrophosphates or sulfates or hemi-succinates, or (d) formation of pharmaceutically acceptable salts, or (e) formation of pharmaceutically acceptable complexes, or (f) synthesis of pharmacologically active polymers, or (g) introduction of hydrophilic moieties, or (h) introduction/exchange of substituents on aromates or side chains, change of substituent pattern, or (i) modification by introduction of isosteric or bioisosteric moieties, or (j) synthesis of homologous compounds, or (k) introduction of branched side chains, or (k) conversion of alkyl substituents to cyclic analogues, or (l) derivatisation of hydroxyl groups to ketales, acetales, or (m) N-acetylation to amides, phenyl-carbamates, or (n) synthesis of Mannich bases, imines, or (o) transformation of ketones or aldehydes to Schiff's bases, oximes, acetales, ketales, enolesters, oxazolidines, thiazolidines; or combinations thereof.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

The present invention further relates to an in vitro method of identifying an inhibitor of sweat formation, comprising the steps of:
a) contacting a secretory sweat gland cell comprising (i) a calcium-activated chloride channel; and (ii) a halide-sensitive cytoplasmic indicator protein; with a test compound;
b) adding to the cells of (a): (b-i) a calcium-elevating agonist; and (b-ii) a halide, preferably iodide;
c) determining the amount of chloride secretion from the secretory sweat gland cell after the contacting with the test compound and the addition of the calcium-elevating agonist and iodide, wherein the amount of chloride secretion is determined based on an alteration of the signal emitted from the halide-sensitive cytoplasmic indicator protein; and
d) comparing the amount of chloride secretion from the secretory sweat gland cell determined in step (c) with the amount of chloride secretion from the secretory sweat gland cell in the absence of the test compound, wherein a decrease in the amount of chloride secretion determined in (c) as compared to the amount of chloride secretion in the absence of the test compound indicates that the test compound is an inhibitor of sweat formation.

All definitions and preferred embodiments provided herein above with regard to the nucleic acid molecule and the protein of the invention apply mutatis mutandis also to this method of identifying an inhibitor of sweat formation.

In a first step, a secretory sweat gland cell is contacted with the compound to be tested. The test compound to be tested as a potential inhibitor may be any of the above defined inhibitory molecules. More preferably, the test compound is selected from the group consisting of a small molecule, an antibody, an aptamer/spiegelmer, an sRNA, an shRNA, an miRNA, a ribozyme or an antisense nucleic acid molecule.

The secretory sweat gland cell may be any secretory sweat gland cell, as long as it comprises both a calcium-activated chloride channel and a halide-sensitive cytoplasmic indicator protein. Accordingly, the secretory sweat gland cell may be a primary cell isolated from an organism of interest or may be an established secretory sweat gland cell line, into which a halide-sensitive cytoplasmic indicator protein has been introduced. A cell may be chosen that endogenously expresses a calcium-activated chloride channel or, in those cases where the cells do not endogenously express such a calcium channel, they may be modified to express said channel. Also envisaged herein is the expression of an exogenous (i.e. experimentally introduced) calcium-activated chloride channel, such as e.g. the nucleic acid molecule/polypeptide of the present invention, in secretory sweat gland cells that already endogenously express a calcium-activated chloride channel. In this case, the nucleic acid molecule of the invention is introduced to increase the expression of the endogenously present calcium-activated chloride channel. Preferably, the nucleic acid molecule of the invention is introduced to achieve an at least 2-fold increase of expression of the endogenously present calcium-activated chloride channel, more preferably an at least 5-fold increase of expression, such as an at least 10-fold increase of expression and even more preferably an at least 20-fold increase of expression, such as an at least 50-fold increase of expression, more preferably an at least 100-fold increase of expression, such as an at least 500-fold increase of expression and most preferably an at least 1000-fold increase of expression.

Accordingly, step (a) of the method of the present invention may comprise an initial step (a-a) comprising introducing into the secretory sweat gland cell a nucleic acid molecule encoding a calcium-activated chloride channel, preferably the nucleic acid molecule of the present invention, in expressible form, i.e. in a form that ensures expression of the corresponding protein in the cell. Suitable regulatory sequences ensuring expression of a protein have been defined herein above. In a second step (a-b) the cell is then contacted with a test compound, as described herein above.

Means and methods to verify whether a cell endogenously expresses a calcium-activated chloride channel are well known in the art and include, for example, the methods of determining the expression level of a protein on the nucleic acid level or on the a mino acid level as detailed herein above.

The calcium-activated chloride channel and/or the halide-sensitive cytoplasmic indicator protein can be introduced into the cell by methods well known to the skilled person, such as e.g. by transfecting, virally infecting or electroporating the cell with a nucleic acid molecule encoding said proteins, microinjection of said proteins or upregulation of an endogenous calcium-activated chloride channel gene by using dTALES (designer transcription activator-like effectors) or other methods described herein above.

Halide-sensitive cytoplasmic indicator proteins are well known in the art (see e.g. (31)) and relates to proteins located in the cytoplasm of (a) cell(s) that are capable of providing a signal upon contact with a halide, which are ions from the $7^{th}$ maingroup of the periodic table (e.g. $F^-$, $Cl^-$, $Br^-$, $I^-$). Halide-sensitive indicator proteins can for example be derived from the yellow fluorescent protein (YFP) (30, 31). A small buried cavity close to the chromophore of the YFP permits incorporation of small anions, preferably halides. The bound halide directly interacts with the chromophore and with the phenol group of thyrosine at position 203 in the cavity via hydrogen bonds (32). Usually, these proteins are also capable of providing a signal upon contact with other anions such as e.g. $NO_3^-$, $SCN^-$, $ClO_4^-$, and other ions, e.g. formate and acetate, although they are typically less sensitive to these anions and ions as compared to halides.

In accordance with the present invention, the halide-sensitive cytoplasmic indicator protein is a fluorescent protein.

The term "fluorescent protein" refers to proteins emitting fluorescent light upon excitation at a specific wavelength. A variety of fluorescent proteins can be used in the present invention. One group of such fluorescent proteins includes Green Fluorescent Protein isolated from Aequorea victoria (GFP), as well as a number of GFP variants, such as cyan fluorescent protein, blue fluorescent protein and in particular yellow fluorescent protein, etc. (Zhang et aL (2002) Nat Rev Mol Cell Biol. 3:906-18; Zimmer (2002) Chem Rev. 102: 759-81).

Another group of fluorescent proteins includes the fluorescent proteins isolated from anthozoans, including without limitation the red fluorescent protein isolated from Discosoma species of coral, DsRed (Matz et al. (1999) Nat Biotechnol. 17:969-73). Monomeric versions of Ds Red are e.g. mRFP or mRFP1 (Campbell et al. (2002) Proc Natl Acad Sci USA. 99:7877-82), mCherry, mOrange or mPlum (Shaner et aL (2004) Nat Biotechnol. 22:1567-72) or TagRFP (Merzlyak et aL (2007) Nat Methods. 4:555-7). Most recently, GFPs from the anthozoans *Renilla reniformis* and *Renilla kollikeri* were described (Ward et al., U.S. Patent Appn. 20030013849).

An increasingly large number of other fluorescent proteins from a number of ocean life forms have recently been described, and the Protein Data Bank currently lists a number of GFP and GFP mutant crystal structures, as well as the crystal structures of various GFP analogues. Related fluorescent proteins with structures inferred to be similar to GFP from corals, sea pens, sea squirts, and sea anemones have been described, and may be used in accordance with the present invention (for reviews, see (Zhang et al. (2002) Nat Rev Mol Cell Biol. 3:906-18; Zimmer (2002) Chem Rev. 102:759-81)).

The group of yellow fluorescent proteins (YFP) are derivatives of GFP containig four point mutations (S65G, V86L, S72A, T203Y). YFP and derivatives thereof were described to be pH sensitive and to have halide-binding properties (30, 31). YFP proteins can therefore be used as genetically encoded intracellular pH sensors or halide detectors. Based on crystallographic data and on rational design, various YFP derivatives with improved spectroscopical properties and improved halide binding sensitivity have been developed (33, 34), such as the YFP-H148Q/I152L, which shows high affinity binding to iodide (2 mM). It is thought that halide-binding supresses the delocalization of the phenolate negative charge of the chromophore, which increases the $pK_a$ value of the chromophore. Since the protonated form of the chromophore is non-fluorescent, YFP fluorescence decreases upon halide binding (32).

In a second step, a calcium-elevating agonist and a halide, preferably iodide, is added to the cells. Non-limiting examples of calcium-elevating agonists are calcium ionophores such as e.g. ionomycin and A23187, purinergic agonists such as e.g. ATP or UTP, cholinergic agonists such as e.g. acetylcholine or carbachol as well as α-adrenergic agents such as e.g. adrenaline. The calcium-elevating agonist leads to the activation of the calcium-activated chloride channel, which in turn results in the efflux of chloride ions. Chloride-efflux leads to an immediate and proportional halide (e.g. iodide) influx because chloride channels are permeable for halides, such as iodide. The different intra- and extracellular concentrations of the halide create an inwardly directed halide gradient, which drives iodide through the activated, iodide permeable chloride channel (35, 36).

The halide inside the cell functionally interacts with the halide-sensitive cytoplasmic indicator protein, which leads to a quenching of the signal provided by the halide-sensitive cytoplasmic indicator protein. The more halide (such as e.g. iodide) flows into the cell, the weaker the signal emitted by the halide-sensitive cytoplasmic indicator protein becomes. This alteration of the signal emitted by the halide-sensitive cytoplasmic indicator protein is determined in a third step of the method of the invention. Due to the fact that the influx of halide into the cell is proportional to the efflux of chloride ions, the halide influx is used as a direct measure for chloride secretion. To determine the amount of chloride secretion, the fluorescence decrease is plotted against time (Δfluorescence/Δtime) and the initial slope of the resulting graph represents the iodide influx rate ($sec^{-1}$), which in turn is directly proportional to the chloride efflux rate, representing the amount of chloride secretion per time. In a fourth step, this amount of chloride secretion determined in the presence of a test compound is compared to the amount of chloride secretion determined in the absence of a said compound. If the test compound is capable of inhibiting a calcium-activated chloride channel, this will be reflected by a reduced amount of chloride secretion from the secretory sweat gland cell. Such an inhibitory compound thus represents an inhibitor of sweat formation.

Steps (a) and (b) of the method of the invention can be carried out subsequently to each other (i.e. first step (a) and then step (b)) or at the same time. Preferably, step (a) is carried out prior to step (b). Subsequently, step (c) is carried out, followed by step (d).

It will be appreciated by the skilled person that prior to carrying out the method of the invention (for example as a step (a-0) prior to step (a)) or in parallel thereto, the signal emitted by the halide-sensitive cytoplasmic indicator protein is determined in the cell in order to establish the signal strength in the cell without the activation of the calcium-activated chloride channel. This step may be carried out once to provide a reference value for future use or may be carried out each time the method is carried out. The signal detected in step (c) is then compared to this reference signal in order to determine the amount of chloride secretion in step (d).

In accordance with this method of the invention, it is possible to identify novel compounds which interfere with the process of primary sweat formation, using a sweat gland cell assay. Excessive and uncontrollable sweating is a medical condition known as hyperhidrosis. Several target sites are currently used to treat hyperhidrosis, as discussed herein above. However, none of the compounds presently available in the art makes use of the potential to directly and specifically target this initial calcium-activated chloride channel-mediated step of sweat secretion. Instead, the presently employed compounds typically function via a physical obstruction of the sweat gland pore and channel. The discovery of a sweat gland-specific TMEM16A isoform and the generation of a sweat gland cell-based assay system described herein permits the high-troughput screening for novel compounds that specifically and efficiently reduce excessive sweating. Such compounds are suitable lead compounds for the development of cosmetic applications, such as in antiperspirants as well as in therapeutic applications, such as e.g. the treatment of hyperhidrosis.

In a preferred embodiment, the fluorescent protein is a hsYFP protein, more preferably the fluorescent protein is the hsYFP represented by SEQ ID NO:3 and is encoded by the exemplary nucleic acid sequence represented in SEQ ID NO:4.

In another preferred embodiment of the method of the invention, the secretory sweat gland cell is a mammalian secretory sweat gland cell.

In accordance with the present invention, the mammal is preferably selected from the group consisting of humans, rodents, dogs, felids, non-human primates, rabbits, pigs, equines and ruminants.

Non-limiting examples of "rodents" are mice, rats, squirrels, chipmunks, gophers, porcupines, beavers, hamsters, gerbils, guinea pigs, degus, chinchillas, prairie dogs, and groundhogs. Preferably, the rodents are mice or rats.

Non-limiting examples of "dogs" include members of the subspecies *canis lupus familiaris* as well as wolves, foxes, jackals, and coyotes. Preferably, the dogs are from the subspecies *canis lupus familiaris* and in particular are selected from beagles or dobermans.

Non-limiting examples of "felides" include members of the two subfamilies: the pantherinae, including lions, tigers, jaguars and leopards and the felinae, including cougars, cheetahs, servals, lynxes, caracals, ocelots and domestic cats.

The term "non-human primates", as used herein, refers to all monkeys including for example cercopithecoid (old world monkey) or platyrrhine (new world monkey) as well as lemurs, tarsiers, apes and marmosets (*Callithrix jacchus*). Preferably, the primates are selected from the group consisting of marmosets as well as guenons, macaques, capuchins and squirrel monkeys.

Examples of "equines" include, without being limiting, horses, donkeys and zebras.

Examples of "ruminants" include, without being limiting, cattle, goats, sheep, giraffes, bison, moose, elk, yaks, water buffalo, deer, camels, alpacas, llamas, antelope, pronghorn, and nilgai. Preferably, the ruminants are selected from the group consisting of cattle, goats and sheep.

In a more preferred embodiment, the mammalian secretory sweat gland cell is a human secretory sweat gland cell.

Human secretory sweat gland cells may for example be primary cells obtained from sweat glands, which were for example isolated from skin biopsies, cell lines established from such primary cells as well as already established cell lines such as e.g. the immortalized sweat gland cell line NCL-SG3 as described in the art, e.g. Lee and Dessi (1989) J Cell Sci, 92, 241-249. Means and methods of obtaining primary cells or establishing cell lines from such primary cells are well known in the art and have been described, e.g. in Lee et al. 1986 (37).

In an even more preferred embodiment, the human secretory sweat gland cell is a cell of the cell line NCL-SG3.

In another preferred embodiment of the method of the invention, the calcium-activated chloride channel is a TMEM16 family member.

The term TMEM16 family, as used herein, relates to a new family of ion channels, consisting of 10 members (TMEM16A-K), which share a conserved domain structure comprised of eight transmembrane segments flanked by distinct N- and C-terminal intracellular domains (38-40). The cytoplasmic domains might serve a regulatory function, because they contain phosphorylation (40) and calmodulin binding sites (41), which may be important for full activation of TMEM16A. Members of the TMEM16 family are found in a variety of different cell types and tissues. Due to alternative splicing, multiple protein isoforms have been described (23, 26).

In a more preferred embodiment, the TMEM16 family member is TMEM16A.

TMEM16A has been previously found to be expressed in different cell types, and each cell type and tissue expresses a characteristic set of various TMEM16A isoforms rather than a single tissue-specific splice variant. These isoforms are characterized by alternatively spliced segments (a, b, c, d, encoded by exons-1, 6b, 13 and 15, respectively), which are located in the N-terminal region and in the first intracellular loop. TMEM16A isoforms can be distinguished by calcium-sensitivity, voltage-dependence and activation/deactivation kinetics (26, 42, 43).

In an even more preferred embodiment, the TMEM16A is a human TMEM16A.

Human TMEM16A (acd) is represented by NCBI Reference Sequence: NM_018043.5 (publication date Jul. 22, 2012).

In another more preferred embodiment, the human TMEM16A is encoded by the nucleic acid molecule of the invention or is the protein of the invention.

Unless otherwise defined, all technical and scientific terms used herein have the same meaning as commonly understood by one of ordinary skill in the art to which this invention pertains. In case of conflict, the present specification, including definitions, will control.

The figures show:

FIG. 1: Expression of TMEM16A in NCL-SG3 cells and in human eccrine sweat glands.

RT-PCR using total RNA isolated from NCL-SG3 cells and from human eccrine sweat glands and TMEM16A specific oligonucleotides revealed TMEM16A transcription in NCL-SG3 cells (A) and also in freshly isolated human eccrine sweat glands (B). RT-PCR products were separated on 2% agarose gels and stained with ethidium bromide. Beta-Actin-specific PCR product of 520 bp was obtained and served as loading control. A 315 bp TMEM16A-specific PCR product was obtained using RNA from NCL-SG3 as wells as from human eccrine sweat glands. No PCR product was obtained when reverse transcriptase (-RT) was omitted.

Figure 2:
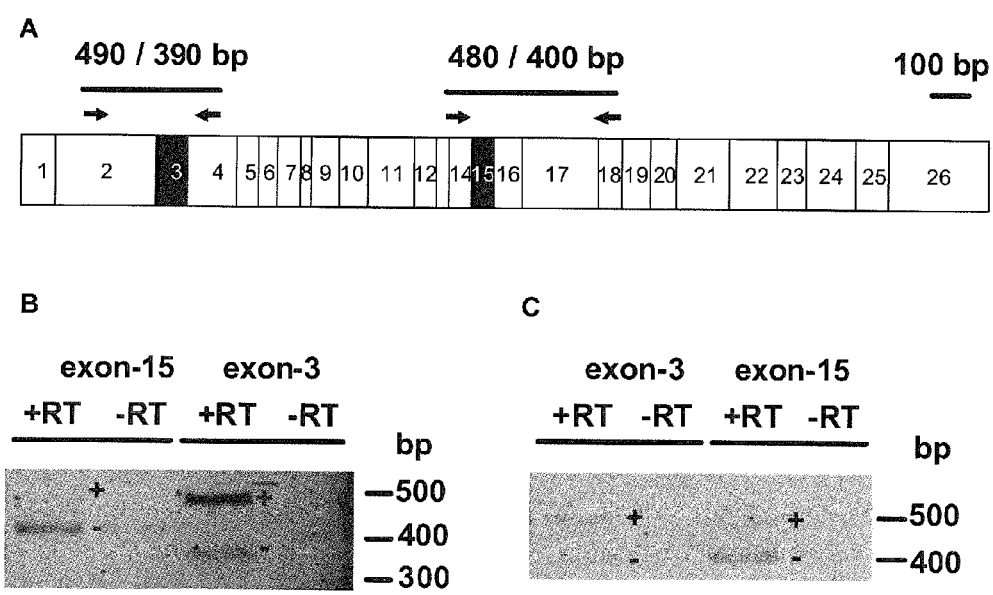

FIG. 2: Alternative splicing of TMEM16A in NCL-SG3 cells and in native human eccrine sweat glands.

(A) Schematic representation of the TMEM16A gene comprising 26 exons (adapted from (26)). Exons 1-26 are boxed; arrows indicate the oligonucleotide binding sites used for RT-PCR analysis. Total RNA was extracted from NCL-SG3 cells (B) and from freshly isolated human eccrine sweat glands (C). RT-PCR products were separated on 2% agarose gels and stained with ethidium bromide. If exon-3 is present (+)/absent (−) a 490/390 bp PCR product is obtained. If exon-15 is present (+)/absent (−) a 475/395 bp PCR product is obtained. TMEM16A splice variants including (+) and excluding (−) exon-3 and exon-15 could be detected in NCL-SG3 cells as well as in human eccrine sweat glands.

FIG. 3: Identification of the novel TMEM16A(acΔe3) splice variant

RT-PCR amplification using oligonucleotides, which amplify full-length TMEM16A (forward 5'-GGCCACGAT-GAGGGTCAACG; reverse 5'-CCTGTAGCTATGCCA-GCGGG) SEQ ID NOS: 5 and 6 and subsequent sequencing of cloned PCR amplification products revealed several TMEM16A full-length variants. Besides TMEM16A(acd) and TMEM16A(ac), which have been described previously, the novel splice variant TMEM16A(acΔe3) could be identified.

(A) Predicted topology of TMEM16A isoforms. All isoforms are composed of eight transmembrane domains but differ in the composition of alternatively spliced segments (a, b, c, d, encoded by exons-1, 6b, 13 and 15, respectively) located in the intracellular N-terminal region. The novel TMEM16A(acΔe3) isoform lacks the short 33 amino acid long, intracellular located, protein segment e3, which is encoded by alternatively spliced exon-3.

(B) Coding and amino acid sequence of TMEM16A(ac) and TMEM16A(acΔe3) lacking exon-3 (bold and underlined).

Figure 4:
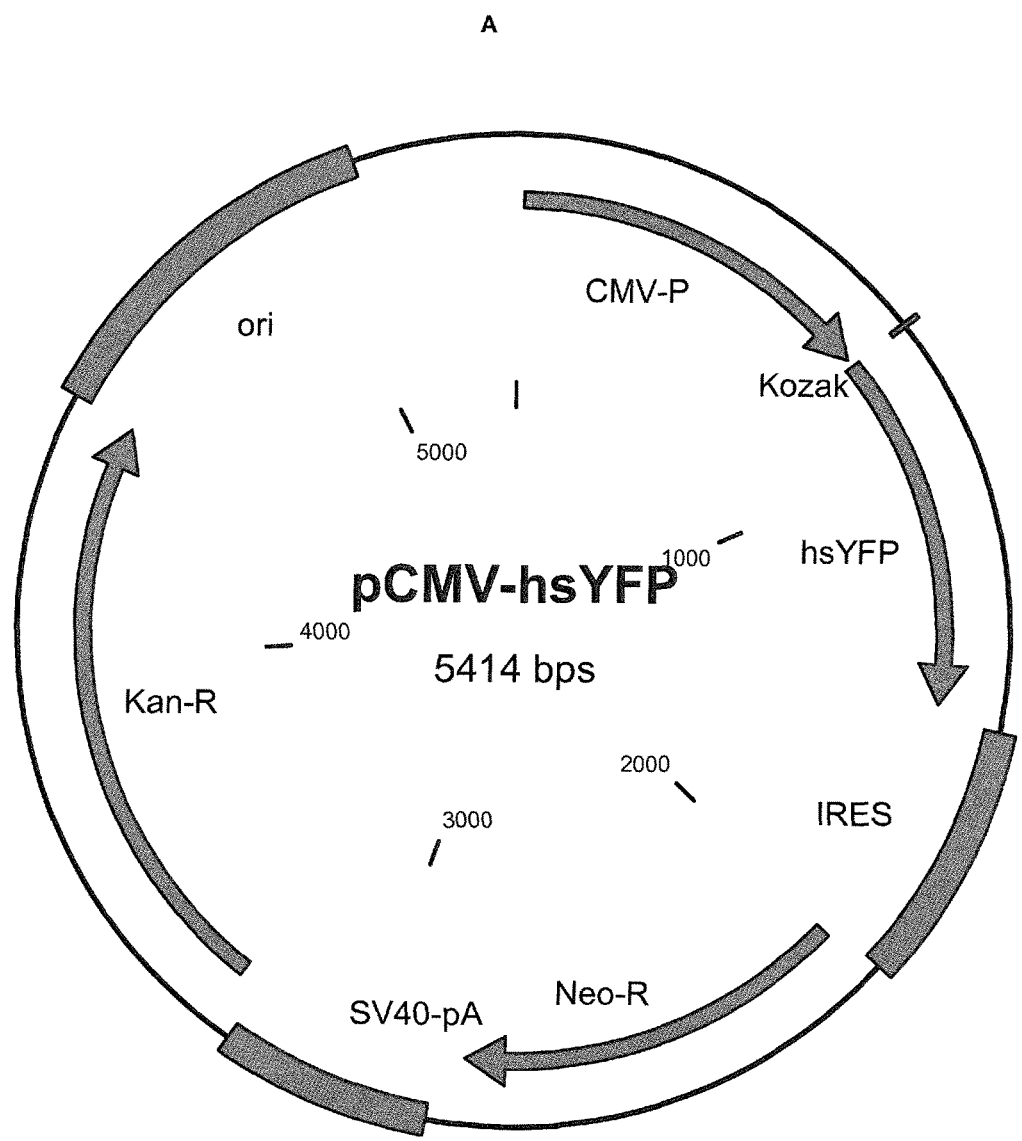

FIG. 4: Plasmid map of the eukaryotic gene expression plasmid pCMV-hsYFP, which permits expression of the $Cl^-/I^-$ flux sensor hsYFP in sweat gland-derived NCL-SG3 cells.

(A) Schematic representation of the vector constructed for the expression of optimized $Cl^-/I^-$ flux sensor hsYFP under transcriptional control of the constitutive CMV promoter (CMV-P) forming a transcription unit with the neomycin resistance gene ($Neo^R$). The hsYFP gene and the $Neo^R$ gene are coupled by an internal ribosomal entry site (IRES) to enable simultaneous translation of both open reading frames located on the same mRNA. Design of the pCMV-hsYFP allows chromosomal integration of the hsYFP-IRES-$Neo^R$ gene expression cassette and $Neo^R$-based selection for stably transfected clones, which express both hsYFP and $Neo^R$. hsYFP sequence contains a consensus Kozak sequence to ensure efficient translation initiation. Ori: Origin of replication; $Kan^R$: Kanamycin resistance gene; SV40-pA: Simian virus 40 polyadenylation signal.

(B) Coding and amino acid sequence of the optimized CU flux sensor hsYFP. The hsYFP gene was optimized by introducing codons to fit human codon usage (underlined) and a consensus Kozak sequence covering the ATG translation start codon (GCCACCATGG) SEQ ID NO:7 to ensure efficient translation initiation.

Figure 5:
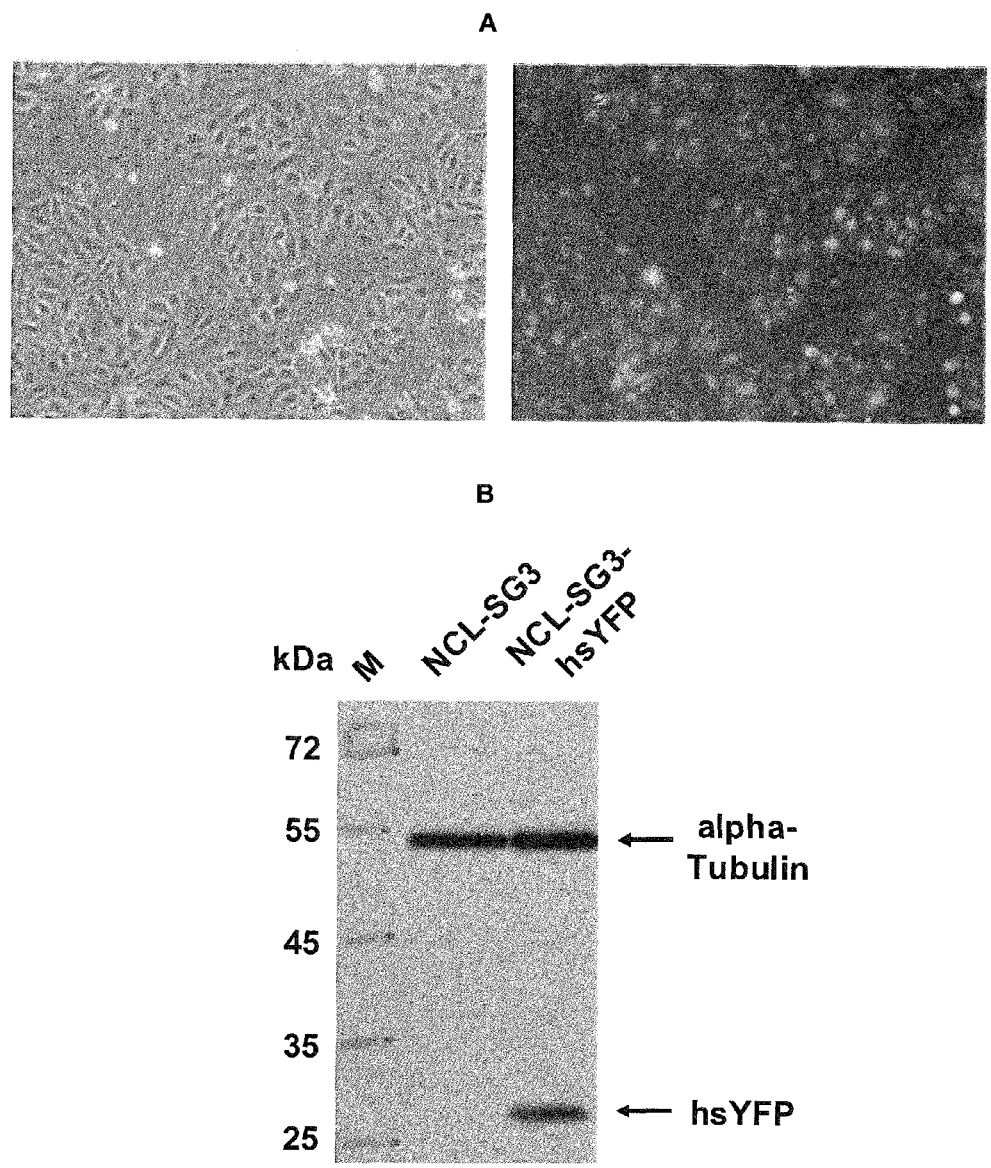
Figure 5:
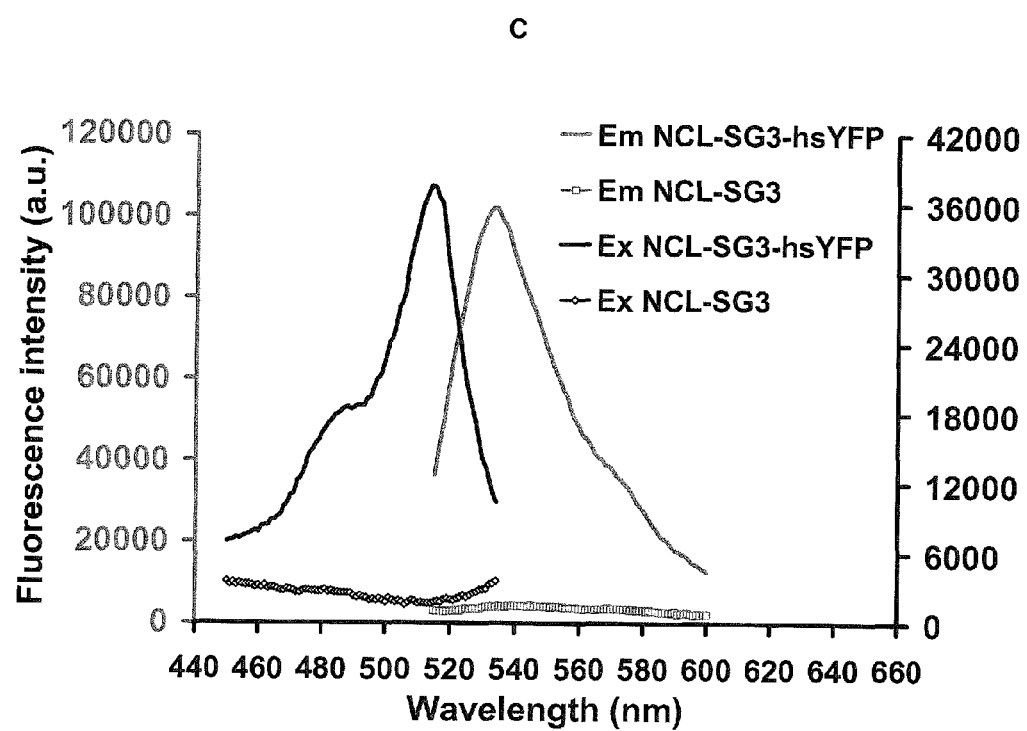

FIG. 5: Characterization of sweat gland-derived CaCC activity sensor cells NCL-SG3-hsYFP.

(A) Microscope images of NCL-SG3-hsYFP cells taken with an Olympus microscope (IX71) coupled to Olympus XC50 digital color camera (XC50). Top image shows a bright field image of NCL-SG3-hsYFP cells. Bottom image shows intracellular localization of hsYFP.

(B) Western blot detection of hsYFP in whole cell lysates using anti-GFP antibody (3H9, ChromoTek). Whole cell lysate proteins were separated by 12% SDS-PAGE and transferred to nitrocellulose membrane. hsYFP was detected only in NCL-SG3-hsYFP cells with an apparent molecular weight of approximately 27 kDa. Alpha-Tubulin was detected using alpha-Tubulin antibody (Sigma) in parental NCL-SG3 cells as well as in NCL-SG3-hsYFP cells and serves as a loading control.

(C) Characteristic in vivo excitation (maxima at 485 and 515 nm) and emission (maximum at 535 nm) spectra of hsYFP in NCL-SG3-hsYFP cells. No fluorescence could be detected in parental NCL-SG3 cells.

Figure 6:
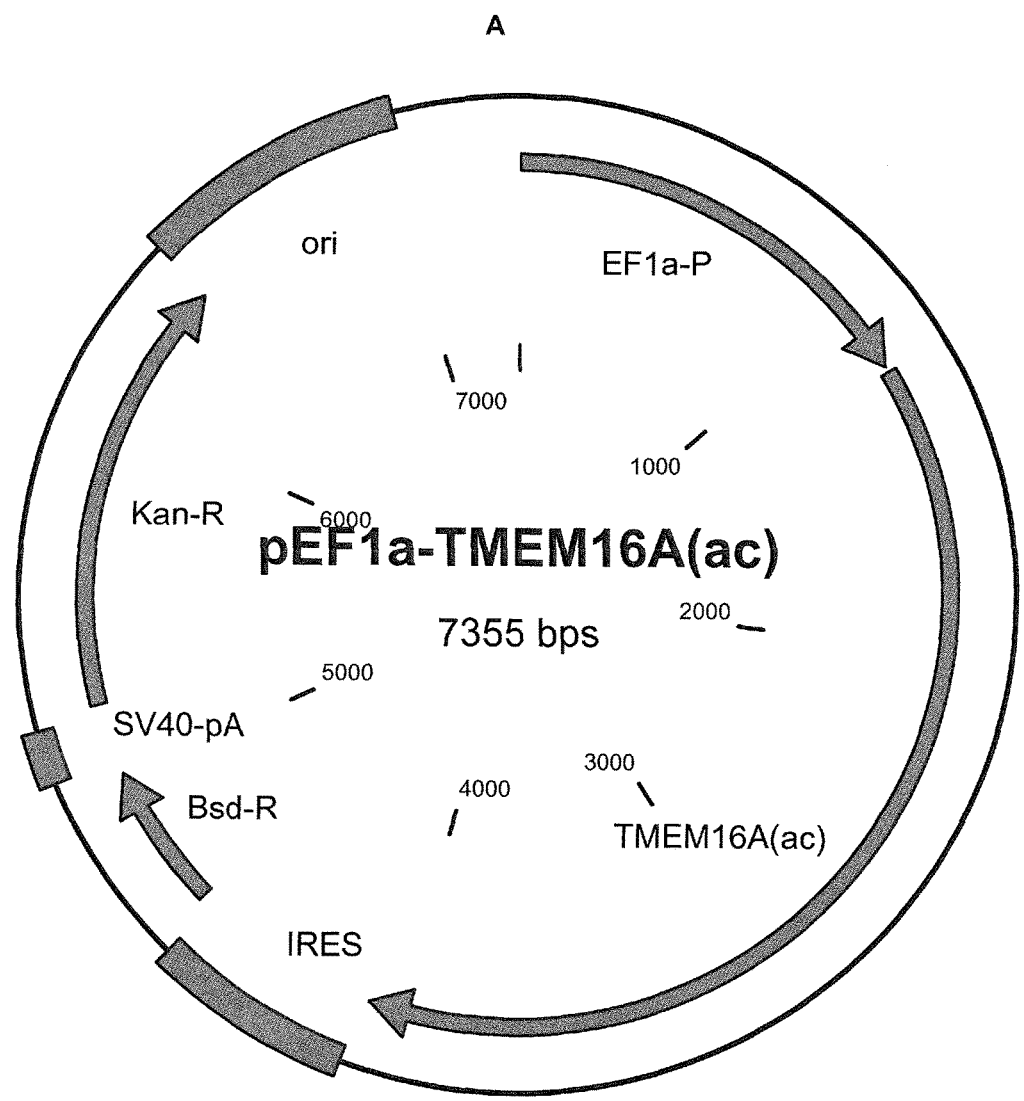
Figure 6:
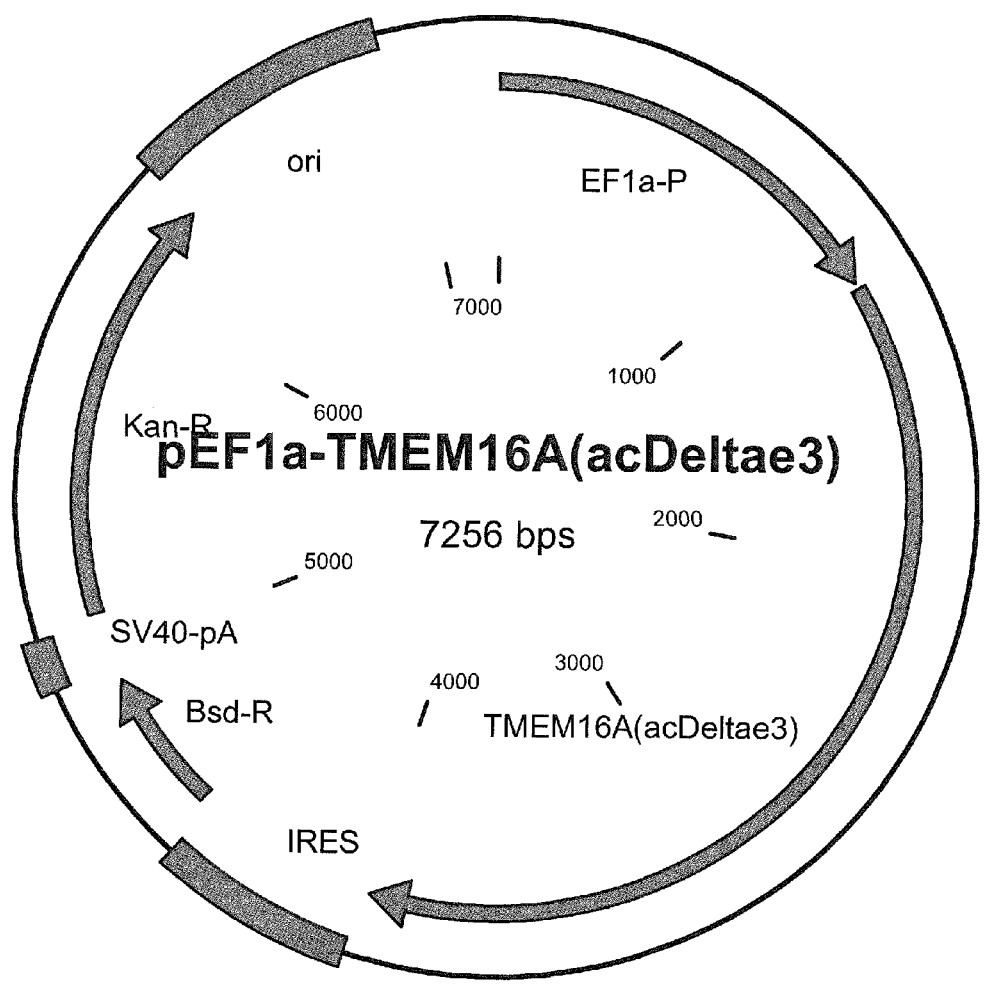
Figure 6:
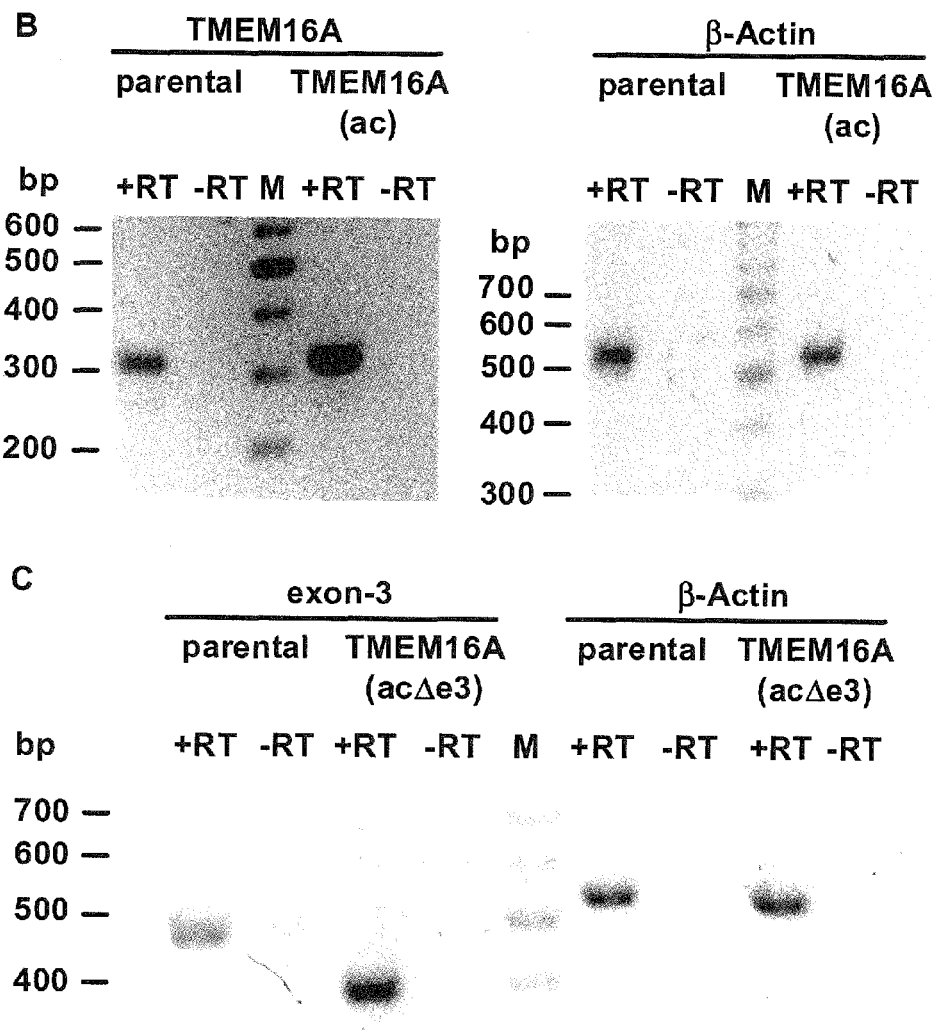

FIG. 6: Generation of NCL-SG3-hsYFP CaCC sensor cells expressing elevated levels of TMEM16A(ac) and TMEM16A(acΔe3)

(A) Plasmid maps of eukaryotic gene expression plasmids pEF1α-TMEM16A(ac) and pEF1α-TMEM 16A(acΔe3), which permit expression of the TMEM16A(ac) and TMEM16A(acΔe3) splice variant in NCL-SG3-hsYFP CaCC sensor cells. Expression of the respective TMEM16A splice variant is under transcriptional control of the constitutive EF1α promoter (EF1α-P) and forms a transcription unit with the blasticidin resistance gene ($Bsd^R$). Both genes are coupled by an internal ribosomal entry site (IRES) to enable efficient translation of both open reading frames located on the same mRNA. Design of the pEF1α-TMEM16A(ac) and pEF1α-TMEM16A (acΔe3) plasmids allows chromosomal integration of the TMEM16A(ac)-IRES-$Bsd^R$ and TMEM16A(acΔe3)-IRES-Bsd $^R$ gene expression cassette and $Bsd^R$-based selection for stably transfected clones, which express both the respective TMEM16A splice variant and $Bsd^R$. Ori: Origin of replication; $Kan^R$: Kanamycin resistance gene; SV40-pA: Simian virus 40 polyadenylation signal.

(B),(C) RT-PCR amplifications to confirm increased expression of TMEM16A(ac) and TMEM16(acΔe3) in stably transfected cells compared to parental NCL-SG3-hsYFP cells. Total RNA was extracted from NCL-SG3-hsYFP-TMEM16A(ac) (B), NCL-SG3-hsYFP-TMEM 16A(acΔe3) (C) and from parental NCL-SG3-hsYFP cells (B and C). PCR products were separated on 2% agarose gels and stained with Midori Green. Beta-Actin-specific PCR product of 520 bp was obtained and served as loading control. No PCR product was obtained when reverse transcriptase (-RT) was omitted (B and C). (B) Significantly more TMEM16A-specific PCR product (315 bp) was obtained using RNA from NCL-SG3-hsYFP-TMEM16A(ac) cells than from parental NCL-SG3-hsYFP cells. (C) In NCL-SG3-TMEM16A(acΔe3) cells exclusively TMEM16A transcripts lacking exon-3 (390 bp) were detected, while in parental NCL-SG3-hsYFP cells TMEM16A transcripts including exon-3 (490 bp) were predominant, which confirms increased TMEM16A(acΔe3) expression in NCL-SG3-TMEM16A(acz\e3) cells. Note that the experimental setup favours detection of predominant transcripts and hence less abundant TMEM16A splice variants can not be detected in contrast to previous analysis (see also FIGS. 2B and C; Example 1 and Example 3).

Figure 7:
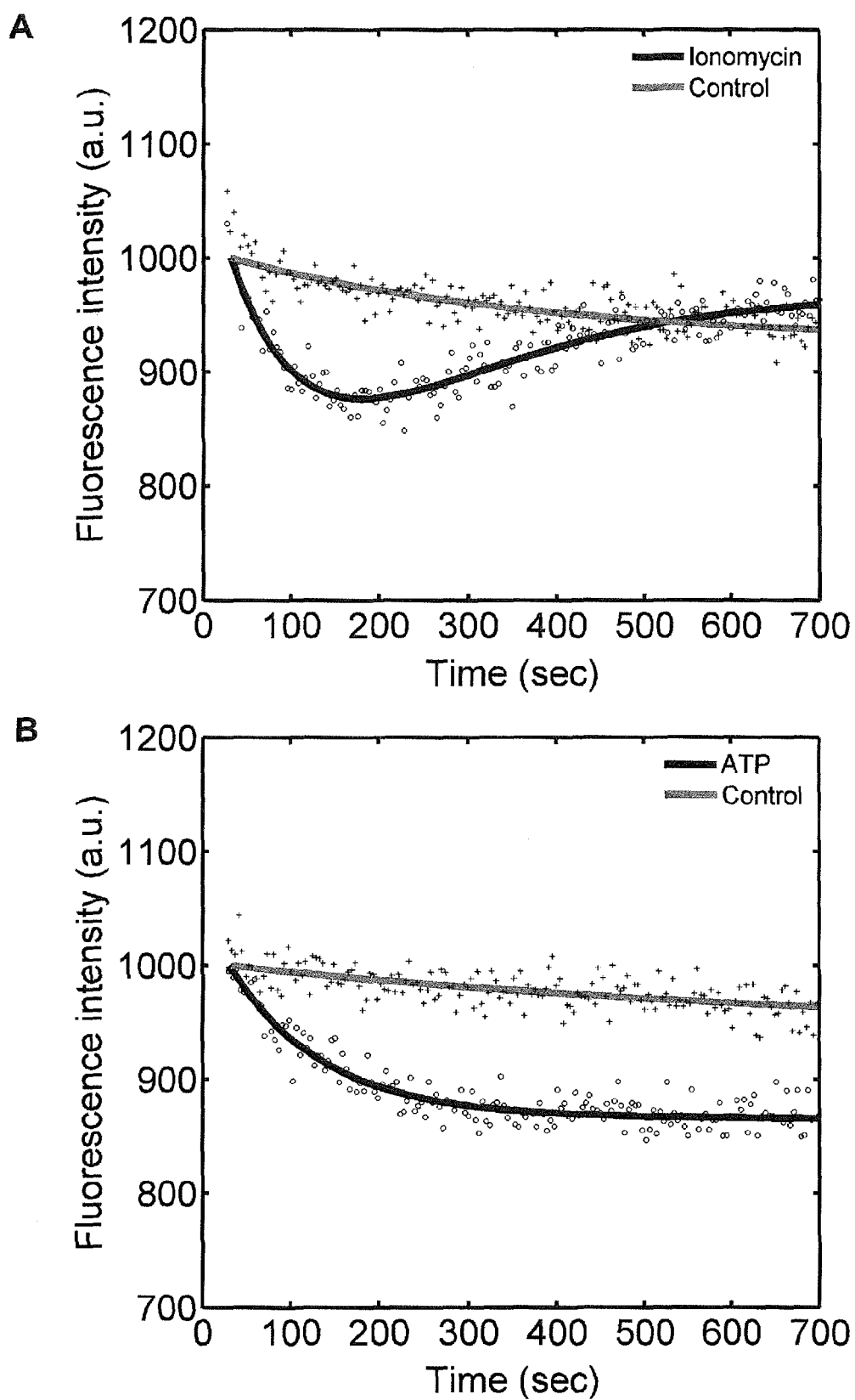
Figure 7:
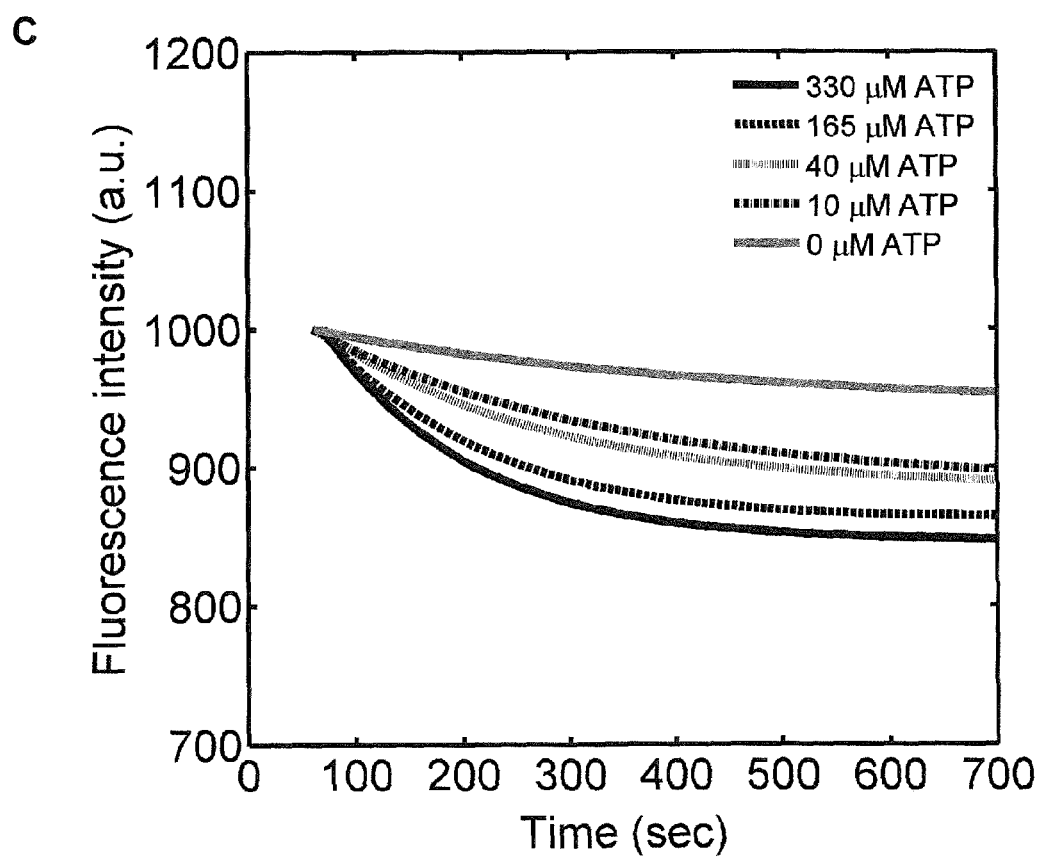

FIG. 7: Detection of $Ca^{2+}$-dependent $Cl^-$ channel activity in sweat gland-derived CaCC activity sensor cells NCL-SG3-hsYFP after treatment with ionomycin and ATP.

$Ca^{2+}$-dependent $Cl^-$ efflux was determined using NCL-SG3-hsYFP cells. $Cl^-$ efflux triggers an immediate and proportional $I^-$ influx, which results in $I^-$-dependent quenching of intracellular hsYFP fluorescence, which was measured and plotted over time.
(A) Addition of the $Ca^{2+}$ ionophore ionomycin (1 μM) results in a quick quenching of the hsYFP fluorescence followed by a slow recovery. Baseline fluorescence is shown when only buffer was added.
(B) Addition of ATP (330 μM) results in a fast quenching of the hsYFP fluorescence without recovery.
(C) ATP-dependent stimulation of $Ca^{2+}$-dependent $Cl^-$ transport in CaCC activity sensor cells NCL-SG 3-hsYFP is dose-dependent. Quenching of intracellular hsYFP fluorescence was measured and plotted over time. Quenching of hsYFP is maximal using 330 μM ATP.

Figure 8:
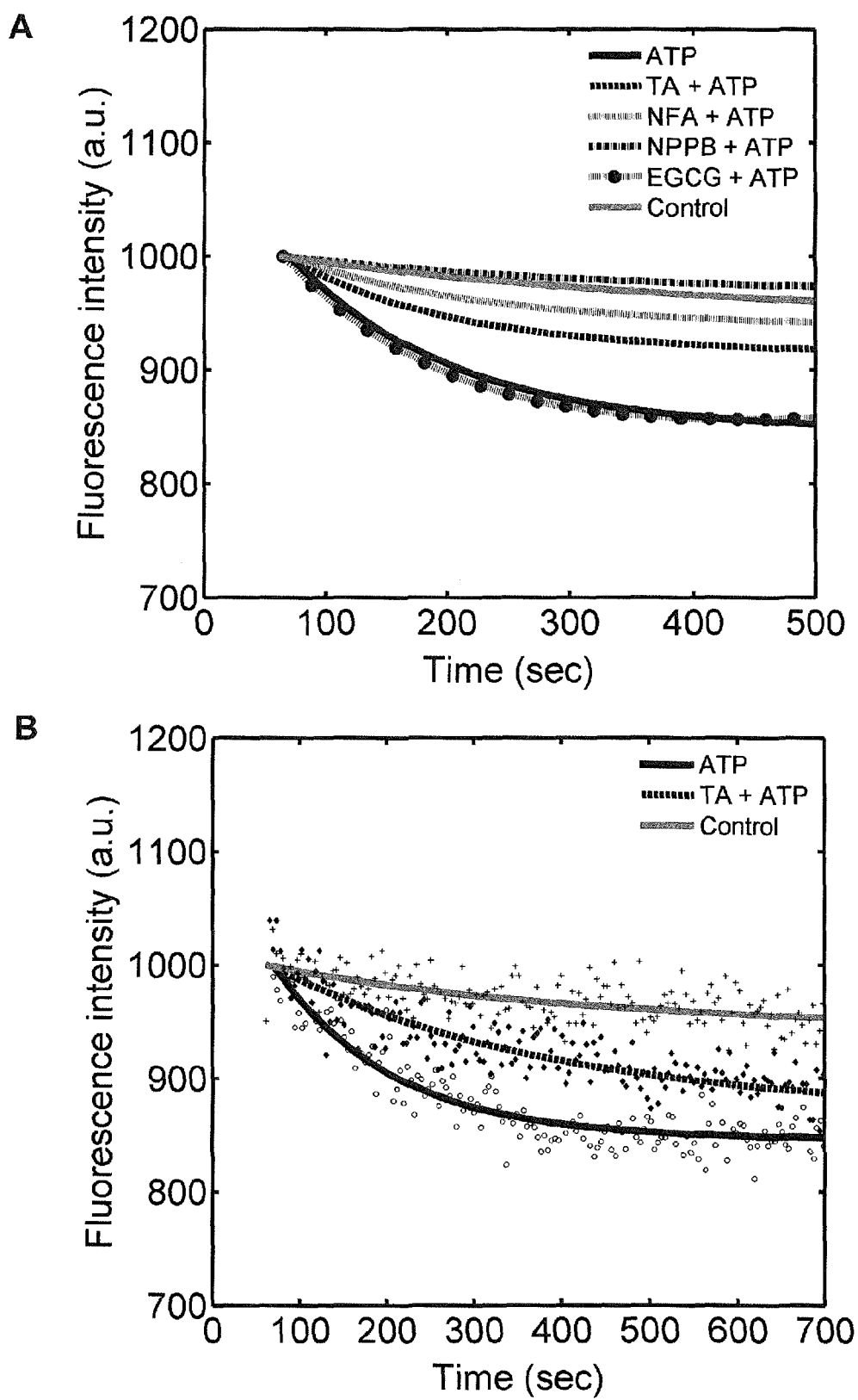

FIG. 8: CaCC inhibitors significantly reduce the $Ca^{2+}$-dependent $Cl^-$ transport in CaCC activity sensor cells NCL-SG3-hsYFP.

Effect of CaCC inhibitors on sweat gland-specific $Ca^{2+}$-dependent CV efflux and proportional $I^-$ influx was determined using NCL-SG3-hsYFP cells. Quenching of intracellular hsYFP fluorescence was measured and plotted over time. Exemplary raw data (B) and fitted curves are shown (A). NCL-SG3-hsYFP cells were incubated with 50 μM tannic acid (TA), 25 μM niflumic acid (NFA), 25 μM 5-nitro-2-(3-phenylpropyl-amino) benzoic acid (NPPB), 100 μM epigallocatechin-3-gallate (EGCG) for 15 min and then stimulated with 330 μM ATP. Pretreatment of the cells with general CaCC inhibitors and with TMEM16A-specific inhibitor tannic acid (TA) resulted in a significant reduction of hsYFP quenching by $Cl^-$ efflux/$I^-$ influx mediated by ATP. Inhibition of $Cl^-$ transport by TMEM16A-specific TA is in the same order of magnitude as NFA and NPPB. EGCG, which effectively inhibits CaCCs in human colonic epithelial cells, had no effect in NCL-SG3-hsYFP cells. These findings further support the notion that sweat gland-derived NCL-SG3 cells possess a cell-type specific CaCC composition and channel properties. Moreover, it indicates that TMEM16A contributes significantly to CaCC activity in NCL-SG3 sweat gland cells.

Figure 9:
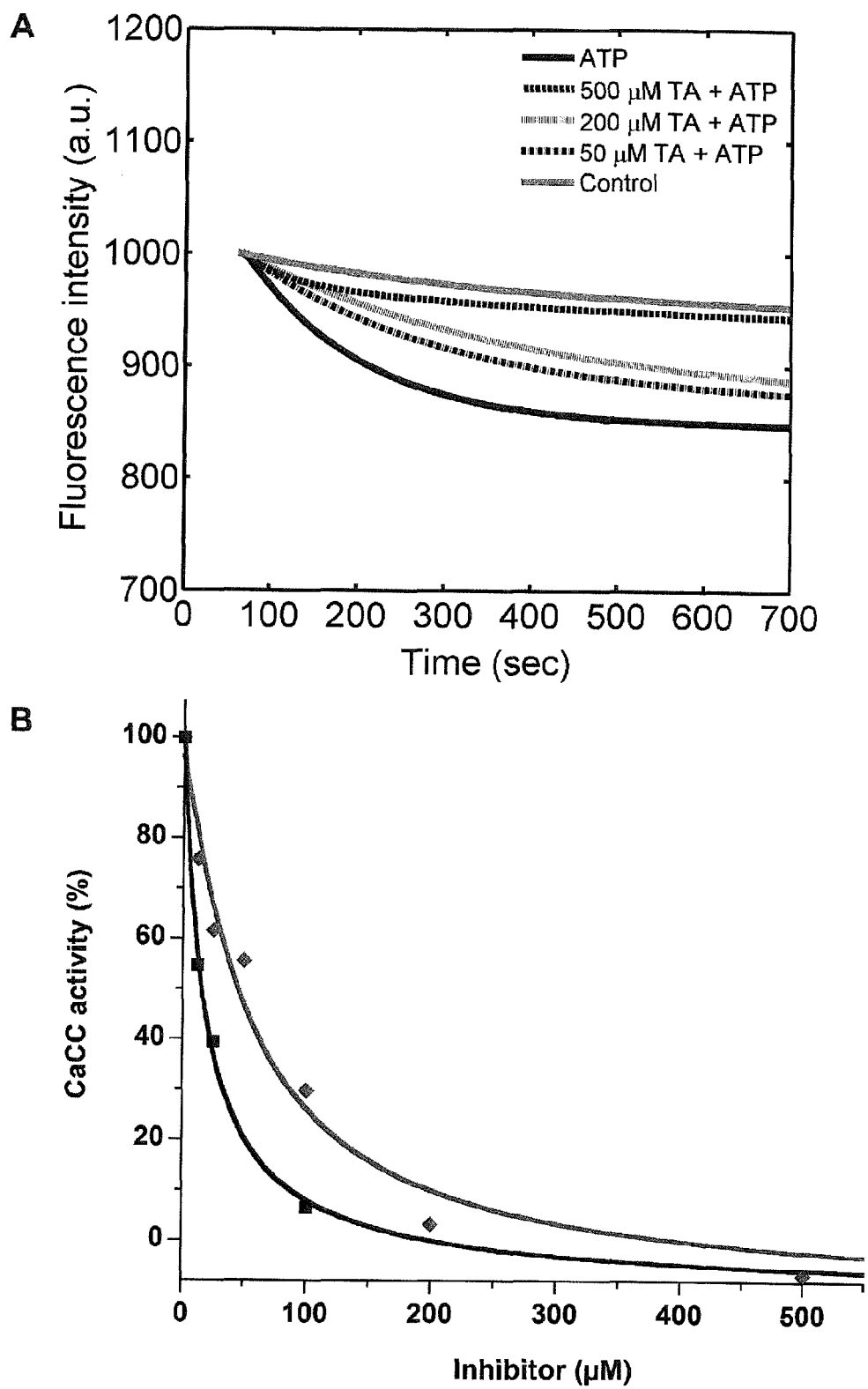

FIG. 9: Characterization of CaCC inhibitors by determining $IC_{50}$ values of CaCC inhibitors in sweat gland-derived CaCC activity sensor cells NCL-SG3-hsYFP.
(A) TMEM16A-specific inhibitor tannic acid significantly reduces $Ca^{2+}$-dependent $Cl^-$ transport in CaCC activity sensor cells NCL-SG3-hsYFP in a dose-dependent manner. Sweat gland-specific $Ca^{2+}$-dependent $Cl^-$ efflux and a proportional $I^-$ influx was determined using NCL-SG3-hsYFP cells. Quenching of intracellular hsYFP fluorescence was measured and plotted over time. Exemplary fitted curves are shown. NCL-SG3-hsYFP cells were incubated with increasing concentrations of tannic acid (TA) and then stimulated with 330 μM ATP. Pretreatment of the cells with TMEM16A-specific inhibitor TA resulted in a dose-dependent reduction of hsYFP quenching after CaCC activation by ATP.
(B) Determination of $IC_{50}$ values of CaCC inhibitors in sweat gland-derived CaCC activity sensor cells NCL-SG3-hsYFP. NCL-SG3-hsYFP cells were incubated with increasing concentrations of CaCC inhibitors and quenching of intracellular hsYFP fluorescence was measured after stimulation with ATP. The rate of r influx ($sec^{-1}$), which is proportional to $Ca^{2+}$-dependent $C^-$ efflux was calculated from the initial slope of the measured hsYFP fluorescence (ΔYFP fluorescence/Δtime) and is a direct measure of CaCC activity. $IC_{50}$ values were determined by plotting the percentage of residual CaCC activity against the individual inhibitor concentration. $IC_{50}$ values for the general CaCC inhibitor NFA (filled squares, black line) and the TMEM16A-specific inhibitor TA (filled diamonds, grey line) are 18.5+/−5.5 μM and 41.0+/−11.2 μM, respectively (p-value<0.01, Student's t-test, two-tailed) and are in the same range as reported previously for endogenous CaCCs and TMEM16A of other cell types (9, 44).

FIG. 10: Characterization of the novel TMEM16A (acΔe3) splice variant in NCL-SG 3-hsYFP CaCC activity sensor cells $Ca^{2+}$-dependent $Cl^-$ secretion mediated by TMEM16A splice variants was quantitatively evaluated using NCL-SG3-hsYFP cells. $Cl^-$ efflux triggers an immediate and proportional $I^-$ influx, which results in $I^-$-dependent quenching of intracellular hsYFP fluorescence, which was measured and plotted over time.

Addition of ATP (330 μM) to NCL-SG3-hsYFP-TMEM16A(ac) (A) and NCL-SG3-hsYFP-TMEM 16A (acΔe3) cells (B), which overexpress either TMEM16A(ac) or TMEM16A(acΔe3) revealed a more efficient quenching of hsYFP compared to NCL-SG3-hsYFP cells (compare FIG. 10A, B and FIG. 7B). Pretreatment of cells with TMEM16A-specific inhibitor tannic acid (TA) resulted in a significant reduction of hsYFP quenching after ATP treatment. These findings indicate that TMEM16A(ac) and TMEM16A(acΔe3) form functional CaCCs and contribute significantly to CaCC activity in NCL-SG3 sweat gland cells.
(C) Untreated NCL-SG3-hsYFP-TMEM16A(acΔe3) cells (Control) showed higher basal quenching of hsYFP compared to parental NCL-SG3-hsYFP cells (Control WT). Pretreatment of (unactivated) NCL-SG3-hsYFP cells with TMEM16A-specific inhibitor TA resulted in a significant reduction of basal hsYFP quenching. These findings show that higher basal $Cl^-$ secretion is mediated by TMEM16A (acΔe3).
(D) Determination of functional properties of TMEM16A splice variants. NCL-SG3-hsYFP, NCL-SG 3-hsYFP-TMEM16A(ac) and NCL-SG3-hsYFP-TMEM16A (acΔe3) cells were untreated (basal activity) or stimulated with ATP (330 μM). Quenching of hsYFP fluorescence was determined. The rate of $I^-$ influx ($sec^{-1}$) was calculated from the initial slope of measured hsYFP fluorescence (ΔYFP fluorescence/Δtime) and is a direct measure of CaCC activity. For better comparison fold changes compared to basal activity of parental cells are shown. TMEM16A(acΔe3) is characterized by a significantly higher basal activity and lower Ca$^{2+}$-induced Cl$^-$ transport ability compared to TMEM16A(ac). All influx rate differences are higly statistically significant, except the basal influx rate of parental and TMEM16A(ac) overexpressing NCL-SG3-hsYFP cells (Student's t-test, two-tailed; *** p-value<0.0001).

The examples illustrate the invention:

EXAMPLE 1

Identification of a Novel TMEM16A Splice Variant in NCL-SG3 Cells and in Human Eccrine Sweat Gland Tissue RT-PCR experiments were performed to identify the CaCC that mediates sweat secretion. Transcription of the candidate TMEM16A was determined in NCL-SG3 cells and in native human eccrine sweat glands. Total RNA from NCL-SG3 cells and from freshly isolated human eccrine sweat glands was extracted using TRIzol® reagent (Invitrogen). cDNA was synthesized by reverse transcription using Poly-dT Primer (ProtoScript M-MuLV First Strand Synthesis Kit, New England Biolabs) according to manufacture's instructions. Diagnostic TMEM16A PCR reactions were performed using TMEM16A isoform specific oligonucleotides (see below) and the Phusion® Flash High-Fidelity PCR Master Mix (Finnzymes). PCR amplification products were separated by 2% agarose gels followed by ethidium bromide staining. RT-PCR analysis revealed that TMEM16A mRNA can be detected in NCL-SG3 cells as well as in human eccrine sweat glands (FIG. 1). By using exon-specific oligonucleotides several alternatively spliced TMEM16A exons were detected, including exon-15, which is already known to be alternatively spliced in other tissues (23, 26) (FIG. 2). Surprisingly, an additional, so far unknown, alternatively spliced exon (exon-3) could be detected (FIG. 2). Moreover, not only the novel splicing event, but also the full-length mRNA of a novel isoform TMEM16A(acΔe3), which lacks exon-3, was identified. TMEM16A(acΔe3) retains the (predicted) overall topology of TMEM16A but lacks protein segments b, d and additionally a 33 amino acid long intracellular segment, which is encoded by exon-3 and hence was termed segment e3 (FIG. 3). These findings indicate that NCL-SG3 cells and native human eccrine sweat gland cells express TMEM16A and share the potentially sweat gland-specific isoform TMEM16A(acΔe3), which appears to be important for CaCC activity and the mechanism of primary sweat formation.

```
Oligonucleotide TMEM16A:
5'-GGAAACAGCGGTACG

Oligonucleotide TMEM16A:
5'-GCGGGATGAAGTCAG

Oligonucleotide exon-3 forward:
5'-GATGCCGAGTGCAAGTATGG

Oligonucleotide exon-3 reverse:
5'-TTTGGGCTGGATGGGATCTG

Oligonucleotide exon-15 forward:
5'-ACGAAGCCAGAGTCTTGGAG

Oligonucleotide exon-15 reverse:
5'-CAAACTTCAGCAGGAAAGCC
```

-continued
```
Oligonucleotide TMEM16A full-length forward:
5'-GGCCACGATGAGGGTCAACG Oligonucleotide TMEM16A full-length reverse:
5'-CCTGTAGCTATGCCAGCGGG
```

In summary, it was shown that TMEM16A transcription is present in NCL-SG3 cells (FIG. 1A) and also in freshly isolated human eccrine sweat glands (FIG. 1B). Therefore, it could be shown that NCL-SG3 cells and isolated human sweat glands express a common set of TMEM16A variants (FIGS. 2B and 2C). Strikingly, a novel and potentially sweat gland-specific splice variant TMEM16A(acΔe3) was discovered (FIG. 3), which is characterized by altered ion channel properties and is considered to be important for fine-tuning Ca$^{2+}$-dependent Cl$^-$ channel activity in secretory sweat gland cells (see Example 5).

EXAMPLE 2

Generation of the Sweat Gland-Derived CaCC Activity Sensor Cell Line NCL-SG 3-hsYFP In order to quantitatively assess the function of TMEM16A splice variants for primary sweat formation, a sweat gland cell-based sensory system to monitor HTS-compatible Cl$^-$ fluxes had to be generated. NCL-SG3 sweat gland cells, which possess the Cl$^-$/I$^-$ flux sensor hsYFP will be a tool to monitor CaCC-dependent Cl$^-$ fluxes. In order to engineer NCL-SG3 cells, the recombinant gene expression plasmid pCMV-hsYFP (FIG. 4) was designed and generated. The previously described coding sequence of the YFP-H148Q/I152L (38, 39, 42, 43, 45) was further modified to improve gene expression in human cells. The following changes were introduced (FIG. 4B): The F46L mutation, which was shown to enhance maturation of YFP (40, 41, 46, 47), was introduced and several codons were adjusted for optimal human codon usage. In addition, the YFP-H148Q/I152L/F46L sequence was further modified to introduce a consensus Kozak sequence covering the ATG translation start (GCCACCATGG) SEQ ID NO:7 to ensure efficient translation initiation. The optimized halide-sensitive YFP (hsYFP) gene including all changes to the DNA sequence was synthesized by Geneart (Regensburg, Germany) and subsequently cloned into proprietary eukaryotic gene expression plasmids (pCMV-hsYFP, FIG. 4A). Expression of the Cl$^-$/I$^-$ flux sensor hsYFP is under transcriptional control of the constitutive CMV promoter and forms a transcription unit with the neomycin resistance gene (Neo$^R$). The hsYFP gene and the Neo$^R$ gene are coupled by an internal ribosomal entry site (IRES) to enable simultaneous translation of both open reading frames located on the same mRNA. Design of the pCMV-hsYFP allows chromosomal integration of the hsYFP-IRES-Neo$^R$ gene expression cassette and Neo$^R$-based selection for stably transfected clones, which express both hsYFP and Neo$^R$.

In order to measure Cl$^-$/I$^-$ flux in vivo, NCL-SG3-hsYFP cells were engineered to functionally produce hsYFP by transfecting NCL-SG3 cells with the linearized plasmid pCMV-hsYFP harboring the hsYFP-IRES-Neo$^R$ gene expression cassette using the Lipofectamine®2000 reagent (Invitrogen) according to manufacture's instructions. Stably transfected clones were selected in the presence of 0.4 mg/ml geneticin and single clones isolated. NCL-SG3 clones expressing hsYFP (FIG. 5A) were confirmed by Western blot detection of hsYFP in whole cell lysates using a monoclonal anti-GFP antibody (3H9, ChromoTek) (FIG.

5B) and by recording the characteristic YFP emission and excitation spectra in living cells (FIG. 5C).

EXAMPLE 3

Expression of TMEM16A Splice Variants in NCL-SG3-hsYFP CaCC Activity Sensor Cells to Monitor $Ca^{2+}$-Dependent $Cl^-$ Efflux To provide additional evidence that TMEM16A is directly involved in mediating $Ca^{2+}$-depending $Cl^-$ efflux in sweat gland cells, a stable NCL-SG3 cell line was generated expressing an increased amounts of TMEM16A(ac) in addition to all endogenous TMEM16A variants (FIG. 6B). The TMEM16A(ac) isoform is found in various tissues and was shown previously to be functional in mammalian cells (26). In contrast, the function of the novel TMEM16A(acΔe3) splice variant is unknown. Therefore, a stable NCL-SG3 cell line was generated expressing an increased amount of TMEM16A(acΔe3) (FIG. 6C).

TMEM16A(ac) and TMEM16A(acΔe3) are present in human eccrine sweat glands and were therefore obtained by RT-PCR amplification using TRIzol® (Invitrogen) extracted RNA from freshly isolated human eccrine sweat glands using oligonucleotides (forward 5'-GGCCACGAT-GAGGGTCAACG; reverse 5'-CCTGTAGCTATGCCA-GCGGG) SEQ ID NOS: 5 and 6, which amplify full-length TMEM16A, and subsequently cloned into the proprietary eukaryotic gene expression plasmid (pEF1α-TMEM16A (ac) and pEF1α-TMEM16A(acΔe3), FIG. 6A). Expression of the TMEM16A splice variant is controlled by the constitutive EF1α promoter and forms a transcription unit with the blasticidin resistance gene ($Bsd^R$). Both genes are coupled by an internal ribosomal entry site (IRES) to enable efficient translation of both open reading frames located on the same mRNA. Design of the pEF1α-TMEM16A(ac) and pEF1α-TMEM 16A(acΔe3) plasmid allows a) chromosomal integration of the TMEM16A-IRES-$Bsd^R$ gene expression cassette and b) $Bsd^R$-based selection for stably transfected clones, which express both TMEM16A and $Bsd^R$. NCL-SG3-hsYFP CaCC sensor cells were transfected with the linearized pEF1α-TMEM16A(ac) or pEF1α-TMEM16A (acΔe3) plasmid harboring the TMEM16A(ac)-IRES-$Bsd^R$ or TMEM16A(acΔe3)-IRES-$Bsd^R$ gene expression cassette using the Lipofectamine® 2000 reagent (Invitrogen) according to manufacture's instructions. Stably transfected clones were selected in the presence of 0.2-0.4 mg/ml geneticin and 2.5-5.0 μg/ml blasticidin and single clones isolated.

RT-PCR experiments were performed to validate overexpression of TMEM16A(ac) and TMEM16A(acΔe3) in single isolated clones (FIGS. 6B and 6C). Total RNA was extracted from NCL-SG3-hsYFP-TMEM16A(ac), NCL-SG3-hsYFP-TMEM16A(acΔe3) and from parental NCL-SG3-hsYFP cells using NucleoSpin® RNA II Kit (Macherey-Nagel) and subsequently used to synthesize cDNA using Poly-dT Primer (ProtoScript M-MuLV First Strand Synthesis Kit, New England Biolabs). PCR products were separated on 2% agarose gels and stained with Midori Green. RT-PCR analysis confirmed overexpression of TMEM16A(ac) and TMEM16A(acΔe3) in the respective stable cell lines compared to endogenous expression in parental NCL-SG3-hsYFP cells. Moreover, overexpression of the TMEM16A(acΔe3) splice variant led to downregulation of all splice variants that include exon-3 (FIG. 6C), indicating a tight regulatory network to ensure sweat gland-specific ion homeostasis. Consequently, NCL-SG 3-hsYFP-TMEM16A(acΔe3) cells are suited for assessing soley the function of the novel TMEM16A(acΔe3) splice variant in the absence of other TMEM16A splice variants in a sweat gland-specific cellular environment.

EXAMPLE 4

Identification of Sweat Gland Specific CaCC and TMEM16A Inhibitors Using NCL-SG3-hsYFP CaCC Activity Sensor Cells In order to proof the suitability of NCL-SG3-hsYFP cells for measuring sweat gland specific CaCC activity, NCL-SG3-hsYFP cells were treated with the $Ca^{2+}$ ionophore ionomycin and with the physiologically relevant $Ca^{2+}$-elevating agent ATP and $Ca^{2+}$-dependent $Cl^-$ secretion was quantitatively evaluated (FIG. 7). Importantly, previously established CaCC inhibitors, such as niflumic acid (NFA) and 5-nitro-2-(3-phenylpropyl-amino) benzoic acid (NPPB) (9), antagonized CaCC-mediated $Cl^-$ efflux in a dose-dependent manner (FIG. 8). In contrast, epigallocatechin-3-gallate (EGCG), which effectively inhibits $Cl^-$ currents in human colonic epithelial cells (44), had no effect on CaCC-mediated $Cl^-$ efflux in NCL-SG3-hsYFP cells (FIG. 8A), highlighting the sweat gland-specific CaCC composition and properties. These findings provide evidence for the first time that activity of CaCCs is mediated by TMEM16A in NCL-SG 3 sweat gland cells. By using a TMEM16A-specific inhibitor (tannic acid) (44) and by overexpressing TMEM16A(ac) in NCL-SG3-hsYFP cells it could be shown that $Ca^{2+}$-dependent $Cl^-$ secretion is mediated by TMEM16A (FIG. 8-10).

Taken together, NCL-SG3-hsYFP cells can be used to monitor $Ca^{2+}$-dependent $Cl^-$ fluxes, which represent the initial step in primary sweat formation in sweat gland cells. In order to identify inhibitors of primary sweat formation, substances were tested for their ability to significantly reduce the $Ca^{2+}$-dependent $Cl^-$ transport in NCL-SG3-hsYFP sweat gland cells. NCL-SG3-hsYFP cells were routinely cultivated in Williams' Medium E supplemented with 9% Fetal Calf Serum, 3.5 mM Glutamine, 9 ng/μl Hydrocortisone, Insulin-Transferrin-Selenium-Supplement (PAA Laboratories) at 37° C. and 5% $CO_2$. For microplate assays, 20,000 cells were seeded in 96-well black-walled, clear bottom microplates (Costar) and cultivated for 2 days until cells reached confluency. Cells were washed three times with 100 μl modified Krebs-Henseleit (KH) buffer (137 mM NaCl, 2.7 mM KCl, 1.2 mM $MgSO_4$, 1.2 mM $KH_2PO_4$, 4.2 mM $NaHCO_3$, 1.3 mM $CaCl_2$, 10 mM HEPES, pH 7.4) and incubated with the test compound in 50 μl KH-buffer for 15 min at 37° C. and 5% $CO_2$. Microplates were transferred into an automated fluorescence plate reader (FlexStation®, Molecular Devices) and cellular hsYFP fluorescence was continuously recorded every 3.5 sec until end of the experiment (excitation at 485 nm, emission at 535 nm, cutoff 515 nm). After baseline-recording for 60 sec, cells were stimulated by addition of $I^-$-solution (KH-buffer replacing NaCl by NaI) containing ionomycin or ATP to establish an extracellular $I^-$ concentration of approximately 90 mM. Addition of ATP and ionomycin resulted in a fast $Ca^{2+}$-dependent $Cl^-$ efflux and proportional $I^-$ influx, which leads to an $I^-$-dependent quenching of intracellular hsYFP fluorescence (FIG. 7). Pretreatment of cells with CaCC inhibitors or test compounds results in a significantly reduced or completely abolished $I^-$-influx (FIGS. 8 and 9). NCL-SG3-hsYFP cells allow quantitative evaluation of in vivo $Cl^-$ channel activity (FIGS. 9 and 10D). To determine the exact rate of $Cl^-$ efflux/$I^-$ influx the hsYFP fluorescence was plotted against time ($\Delta$YFP fluorescence/$\Delta$time). The initial slope of the resulting graph represents the I$^-$ influx rate (sec$^{-1}$), which was derived from a least-square fit of a five-parametric exponential equation YFP fluorescence(t)=$p_1$+$p_2$·exp(-$p_3$·t)-$p_4$·exp(-$p_5$·t) with free parameters $p_1$ to $p_5$ and time t to the raw fluorescence data. Subsequently, the arctan of the initial slope was used as a measure of Ca$^{2+}$-dependent ion channel activity. To assess the potency of test compounds, IC$_{50}$ values were determined by plotting the percentage of residual activity (100·(slope$_{inhibitor}$-slope$_{control}$)/(slope$_{activator}$-slope$_{control}$)) against the individual inhibitor concentration (FIG. 9). IC$_{50}$ values for the general CaCC inhibitor NFA and the TMEM16A-specific inhibitor TA are 18.5+/−5.5 µM and 41.0+/−11.2 µM, respectively (p-value<0.01, Student's t-test) and are in the same range as reported previously for endogenous CaCCs and TMEM16A of other cell types (9, 44). In summary, the present NCL-SG3-hsYFP system allows a quantitative measurement of CaCC and TMEM16A-dependent secretory processes in sweat gland cells in a HTS-compatible format. Therefore it is suitable to identifying sweat gland specific, novel antiperspirants in a high-throughput array format.

EXAMPLE 5

Characterization of the Novel TMEM16A(Ac$\Delta$e3) Splice Variant in NCL-SG3-hsYFP CaCC Activity Sensor Cells Exclusion of protein segment e3 might alter ion channel properties of the novel TMEM16A(ac$\Delta$e3) splice variant, which in turn may have important functional consequences for Ca$^{2+}$-dependent Cl$^-$ fluxes in secretory sweat gland cells. To characterize the ion channel properties of the novel splice variant, NCL-SG3-hsYFP cells, which express an increased amount of either TMEM16A(ac) or TMEM16A(ac$\Delta$e3), were generated (see Example 3) and Ca$^{2+}$-dependent Cl$^-$ secretion mediated by the splice variants was quantitatively evaluated. Importantly, overexpression of either splice variant enhances Ca$^{2+}$-dependent Cl$^-$ secretion, which could be inhibited by using a TMEM16A-specific inhibitor (tannic acid), showing that both splice variants form functional CaCCs in NCL-SG3-hsYFP cells (FIG. 10). But strikingly, the splice variants differ in important ion channel properties such as their basal activity and the speed of Ca$^{2+}$-dependent Cl$^-$ secretion (FIG. 10). In particular, the novel splice variant is characterized by a roughly 5-fold higher basal Cl$^-$ permeability compared to TMEM16A(ac) and a lower ATP-induced activity (2-fold vs. 10-fold compared to TMEM16A (ac)). These findings clearly show that the novel TMEM16A (ac$\Delta$e3) splice variant found in human eccrine sweat gland cells is indeed forming a functional CaCC, and, most importantly, differs in key ion channel properties.

Taken together, these data provide evidence for a sweat gland-specific portfolio of TMEM16A isoforms, which differ in their channel properties. As a consequence, highly specific Cl$^-$ currents are generated that meet the exact needs of the secretory sweat gland cell. Therefore, the discovery of the novel TMEM16A(ac$\Delta$e3) splice variant and the generation of the NCL-SG3-hsYFP CaCC activity sensor cell line permits for the first time the identification of highly specific inhibitors of sweat formation.

FURTHER REFERENCES

1. Saga, K. (2002) Structure and function of human sweat glands studied with histochemistry and cytochemistry. *Prog Histochem Cytochem*, 37, 323-386.
2. Sato, K. and Sato, F. (1981) Pharmacologic responsiveness of isolated single eccrine sweat glands. *The American journal of physiology*, 240, R44-51.
3. Ko, W. H., O'Dowd, J. J., Pediani, J. D., Bovell, D. L., Elder, H. Y., Jenkinson, D. M. and Wilson, S. M. (1994) Extracellular ATP can activate autonomic signal transduction pathways in cultured equine sweat gland epithelial cells. *J Exp Biol*, 190, 239-252.
4. Sato, K., Ohtsuyama, M., Suzuki Y. and Sato F. (1991) In HP., S. N. a. B. (ed.), *Pathophysiology of Dermatologic Diseases*. McGraw-Hill Inc., pp. 211-234.
5. Wilson, S. M., Ko, W. H., Pediani, J. D., Rakhit, S., Nichol, J. A. and Bovell, D. L. (1995) Calcium-dependent regulation of membrane ion permeability in a cell line derived from the equine sweat gland epithelium. *Comp Biochem Physiol A Physiol*, 111, 215-221.
6. Sato, K. and Sato, F. (1981) Role of calcium in cholinergic and adrenergic mechanisms of eccrine sweat secretion. *The American journal of physiology*, 241, C113-120.
7. Sato, K. and Sato, F. (1988) Relationship between quin2-determined cytosolic [Ca2+] and sweat secretion. *The American journal of physiology*, 254, C310-317.
8. Hartzell, C., Putzier, I. and Arreola, J. (2005) Calcium-activated chloride channels. *Annu Rev Physiol*, 67, 719-758.
9. Jentsch, T. J., Stein, V., Weinreich, F. and Zdebik, A. A. (2002) Molecular structure and physiological function of chloride channels. *Physiol Rev*, 82, 503-568.
10. Sato, K. (1984) Differing luminal potential difference of cystic fibrosis and control sweat secretory coils in vitro. *The American journal of physiology*, 247, R646-649.
11. Lee, C. M. and Dessi, J. (1989) NCL-SG3: a human eccrine sweat gland cell line that retains the capacity for transepithelial ion transport. *Journal of cell science*, 92 (Pt 2), 241-249.
12. Servetnyk, Z. and Roomans, G. M. (2007) Chloride transport in NCL-SG3 sweat gland cells: channels involved. *Exp Mol Pathol*, 83, 47-53.
13. Mork, A. C., von Euler, A., Roomans, G. M. and Ring, A. (1996) cAMP-induced chloride transport in NCL-SG3 sweat gland cells. *Acta Physiol Scand*, 157, 21-32.
14. Wilson, S. M., Whiteford, M. L., Bovell, D. L., Pediani, J. D., Ko, W. H., Smith, G. L., Lee, C. M. and Elder, H. Y. (1994) The regulation of membrane 1251- and 86Rb+ permeability in a virally transformed cell line (NCL-SG3) derived from the human sweat gland epithelium. *Exp Physiol*, 79, 445-459.
15. Ring, A., Mork, A. C. and Roomans, G. M. (1995) Calcium-activated chloride fluxes in cultured NCL-SG3 sweat gland cells. *Cell Biol Int*, 19, 265-278.
16. Eggermont, J. (2004) Calcium-activated chloride channels: (un)known, (un)loved? *Proc Am Thorac Soc*, 1, 22-27.
17. Worle, B., Rapprich, S. and Heckmann, M. (2007) Definition and treatment of primary hyperhidrosis. *J Dtsch Dermatol Ges*, 5, 625-628.
18. Clark, C. (2006) Sweating and hyperhidrosis. *The Pharmaceutical Journal*, 276.
19. Darbre, P. D. (2005) Aluminium, antiperspirants and breast cancer. *Journal of inorganic biochemistry*, 99, 1912-1919.
20. Garg, S., Loghdey, S. and Gawkrodger, D. J. (2010) Allergic contact dermatitis from aluminium in deodorants. *Contact dermatitis*, 62, 57-58.
21. Namer, M., Luporsi, E., Gligorov, J., Lokiec, F. and Spielmann, M. (2008) [The use of deodorants/antiperspi- 21. rants does not constitute a risk factor for breast cancer]. *Bulletin du cancer*, 95, 871-880.
22. Tester, M. (1997) Techniques for studying ion channels: an introduction. *Journal of experimental botany*, 48 Spec No, 353-359.
23. Caputo, A., Caci, E., Ferrera, L., Pedemonte, N., Barsanti, C., Sondo, E., Pfeffer, U., Ravazzolo, R., Zegarra-Moran, O. and Galietta, L. J. (2008) TMEM16A, a membrane protein associated with calcium-dependent chloride channel activity. *Science*, 322, 590-594.
24. Schroeder, B. C., Cheng, T., Jan, Y. N. and Jan, L. Y. (2008) Expression cloning of TMEM16A as a calcium-activated chloride channel subunit. *Cell*, 134, 1019-1029.
25. Yang, Y. D., Cho, H., Koo, J. Y., Tak, M. H., Cho, Y., Shim, W. S., Park, S. P., Lee, J., Lee, B., Kim, B. M. et al. (2008) TMEM16A confers receptor-activated calcium-dependent chloride conductance. *Nature*, 455, 1210-1215.
26. Ferrera, L., Caputo, A., Ubby, I., Bussani, E., Zegarra-Moran, O., Ravazzolo, R., Pagani, F. and Galietta, L. J. (2009) Regulation of TMEM16A chloride channel properties by alternative splicing. *The Journal of biological chemistry*, 284, 33360-33368.
27. Namkung, W., Phuan, P. W. and Verkman, A. S. TMEM16A inhibitors reveal TMEM16A as a minor component of calcium-activated chloride channel conductance in airway and intestinal epithelial cells. *The Journal of biological chemistry*, 286, 2365-2374.
28. O'Driscoll, K. E., Pipe, R. A. and Britton, F. C. Increased complexity of Tmem16a/Anoctamin 1 transcript alternative splicing. *BMC Mol Biol*, 12, 35.
29. Ferrera, L., Scudieri, P., Sondo, E., Caputo, A., Caci, E., Zegarra-Moran, O., Ravazzolo, R. and Galietta, L. J. A minimal isoform of the TMEM16A protein associated with chloride channel activity. *Biochim Biophys Acta*, 1808, 2214-2223.
30. Jayaraman, S., Haggie, P., Wachter, R. M., Remington, S. J. and Verkman, A. S. (2000) Mechanism and cellular applications of a green fluorescent protein-based halide sensor. *The Journal of biological chemistry*, 275, 6047-6050.
31. Wachter, R. M. and Remington, S. J. (1999) Sensitivity of the yellow variant of green fluorescent protein to halides and nitrate. *Curr Biol*, 9, R628-629.
32. Wachter, R. M., Yarbrough, D., Kallio, K. and Remington, S. J. (2000) Crystallographic and energetic analysis of binding of selected anions to the yellow variants of green fluorescent protein. *Journal of molecular biology*, 301, 157-171.
33. Galietta, L. J., Haggie, P. M. and Verkman, A. S. (2001) Green fluorescent protein-based halide indicators with improved chloride and iodide affinities. *FEBS letters*, 499, 220-224.
34. Nagai, T., Ibata, K., Park, E. S., Kubota, M., Mikoshiba, K. and Miyawaki, A. (2002) A variant of yellow fluorescent protein with fast and efficient maturation for cell-biological applications. *Nature biotechnology*, 20, 87-90.
35. Galietta, L. V., Jayaraman, S. and Verkman, A. S. (2001) Cell-based assay for high-throughput quantitative screening of CFTR chloride transport agonists. *American journal of physiology*, 281, C1734-1742.
36. Verkman, A. S. and Galietta, L. J. (2009) Chloride channels as drug targets. *Nature reviews*, 8, 153-171.
37. Lee, C. M., Carpenter, F., Coaker, T. and Kealey, T. (1986) The primary culture of epithelia from the secretory coil and collecting duct of normal human and cystic fibrotic eccrine sweat glands. *Journal of cell science*, 83, 103-118.
38. Galietta, L. J. (2009) The TMEM16 protein family: a new class of chloride channels? *Biophys J*, 97, 3047-3053.
39. Hartzell, H. C., Yu, K., Xiao, Q., Chien, L. T. and Qu, Z. (2009) Anoctamin/TMEM16 family members are Ca2+-activated Cl- channels. *J Physiol*, 587, 2127-2139.
40. Kunzelmann, K., Kongsuphol, P., Aldehni, F., Tian, Y., Ousingsawat, J., Warth, R. and Schreiber, R. (2009) Bestrophin and TMEM16-Ca(2+) activated Cl(−) channels with different functions. *Cell calcium*, 46, 233-241.
41. Tian, Y., Kongsuphol, P., Hug, M., Ousingsawat, J., Witzgall, R., Schreiber, R. and Kunzelmann, K. Calmodulin-dependent activation of the epithelial calcium-dependent chloride channel TMEM16A. *Faseb J*, 25, 1058-1068.
42. Mazzone, A., Bernard, C. E., Strege, P. R., Beyder, A., Galietta, L. J., Pasricha, P. J., Rae, J. L., Parkman, H. P., Linden, D. R., Szurszewski, J. H. et al. (2011) Altered expression of Ano1 variants in human diabetic gastroparesis. *The Journal of biological chemistry*, 286, 13393-13403.
43. Xiao, Q., Yu, K., Perez-Cornejo, P., Cui, Y., Arreola, J. and Hartzell, H. C. Voltage- and calcium-dependent gating of TMEM16A/Ano1 chloride channels are physically coupled by the first intracellular loop. *Proc Natl Acad Sci USA*, 108, 8891-8896.
44. Namkung, W., Thiagarajah, J R., Phuan, P. W. and Verkman, A. S. Inhibition of Ca2+-activated Cl- channels by gallotannins as a possible molecular basis for health benefits of red wine and green tea. *Faseb J*, 24, 4178-4186.

The invention claimed is:

1. A vector comprising a nucleic acid molecule encoding a protein capable of forming a calcium-activated chloride channel, wherein said nucleic acid molecule comprises or consists of (a) a nucleic acid molecule encoding a protein having the amino acid sequence of SEQ ID NO:1;

(b) a nucleic acid molecule having the DNA sequence of SEQ ID NO:2;

(c) a nucleic acid molecule having the sequence of SEQ ID NO:2, wherein each thymine is replaced by uracil;

(d) a nucleic acid molecule encoding a protein having at least 97% sequence identity to the protein of (a); or (e) a nucleic acid molecule that is degenerate with respect to the nucleic acid molecule of (b), or (c), wherein the nucleic acid molecule of (a), (b), (c), (d), or (e) is inserted into the vector such that a translational fusion with another nucleic acid molecule is generated.

2. A host cell or a non-human host transformed with the vector of claim 1.

3. A method for the production of a protein capable of forming a calcium-activated chloride channel comprising culture of the host cell of claim 2 under suitable conditions and isolation of the calcium-activated chloride channel molecule produced.

4. An in vitro method of identifying an inhibitor of sweat formation, comprising the steps of:

a) contacting a secretory sweat gland cell comprising
   (i) a calcium-activated chloride channel, wherein the calcium-activated chloride channel is the human TMEM16A encoded by a nucleic acid molecule encoding a protein capable of forming a calcium-activated chloride channel, wherein said nucleic acid molecule comprises or consists of
      (a) a nucleic acid molecule encoding a protein having the amino acid sequence of SEQ ID NO:1;
      (b) a nucleic acid molecule having the DNA sequence of SEQ ID NO:2;
      (c) a nucleic acid molecule having the sequence of SEQ ID NO:2, wherein each thymine is replaced by uracil;
      (d) a nucleic acid molecule encoding a protein having at least 97% sequence identity to the protein of (a); or
      (e) a nucleic acid molecule that is degenerate with respect to the nucleic acid molecule of (b), or (c); and
   (ii) a halide-sensitive cytoplasmic indicator protein; with a test compound;

b) adding to the cells of (a):
   b-i) a calcium-elevating agonist; and
   b-ii) a halide;

c) determining the amount of chloride secretion from the secretory sweat gland cell after the contacting with the test compound and the addition of the calcium-elevating agonist and iodide, wherein the amount of chloride secretion is determined based on an alteration of the signal emitted from the halide-sensitive cytoplasmic indicator protein; and d) comparing the amount of chloride secretion from the secretory sweat gland cell determined in step (c) with the amount of chloride secretion from the secretory sweat gland cell in the absence of the test compound, wherein a decrease in the amount of chloride secretion determined in (c) as compared to the amount of chloride secretion in the absence of the test compound indicates that the test compound is an inhibitor of sweat formation.

5. The method of claim 4, wherein the halide-sensitive cytoplasmic indicator protein is a fluorescent protein.

6. The method of claim 4, wherein the secretory sweat gland cell is a mammalian secretory sweat gland cell.

7. The method of claim 6, wherein the mammalian secretory sweat gland cell is a human secretory sweat gland cell.

8. The method of claim 7, wherein the human secretory sweat gland cell is a cell of the cell line NCL-SG3.

9. The method of claim 5, wherein the secretory sweat gland cell is a mammalian secretory sweat gland cell.

10. The method of claim 9, wherein the mammalian secretory sweat gland cell is a human secretory sweat gland cell.

11. The method of claim 10, wherein the human secretory sweat gland cell is a cell of the cell line NCL-SG3.

12. The method of claim 4, wherein the halide is iodide.

13. The vector of claim 1, wherein the other nucleic acid is encoding a protein that increases the solubility and/or facilitates the purification of the binding molecule encoded by the nucleic acid molecule of (a) or a protein of interest that is to be observed by fluorescence imaging.

* * * * *

SEQUENCE LISTING

<160> NUMBER OF SEQ ID NOS: 13

<210> SEQ ID NO 1
<211> LENGTH: 927
<212> TYPE: PRT
<213> ORGANISM: Homo sapiens

<400> SEQUENCE: 1

Met Arg Val Asn Glu Lys Tyr Ser Thr Leu Pro Ala Glu Asp Arg Ser
1               5                   10                  15

Val His Ile Ile Asn Ile Cys Ala Ile Glu Asp Ile Gly Tyr Leu Pro
            20                  25                  30

Ser Glu Gly Thr Leu Leu Asn Ser Leu Ser Val Asp Pro Asp Ala Glu

```
            35                  40                  45
Cys Lys Tyr Gly Leu Tyr Phe Arg Asp Gly Arg Lys Val Asp Tyr
 50                  55                  60

Ile Leu Val Tyr His His Lys Arg Pro Ser Gly Asn Arg Thr Leu Val
 65                  70                  75                  80

Arg Arg Val Gln His Ser Asp Thr Pro Ser Gly Ala Arg Ser Val Lys
                 85                  90                  95

Gln Asp His Pro Leu Pro Gly Lys Gly Ala Ser Leu Asp Ala Gly Ser
                100                 105                 110

Gly Glu Pro Pro Met Asp Tyr His Glu Asp Lys Arg Phe Arg Arg
            115                 120                 125

Glu Glu Tyr Glu Gly Asn Leu Leu Glu Ala Gly Leu Glu Leu Glu Arg
            130                 135                 140

Asp Glu Asp Met Tyr His Ile Asn Glu Thr Arg Gly Leu Leu Lys Lys
145                 150                 155                 160

Ile Asn Ser Val Leu Gln Lys Ile Thr Asp Pro Ile Gln Pro Lys Val
                165                 170                 175

Ala Glu His Arg Pro Gln Thr Met Lys Arg Leu Ser Tyr Pro Phe Ser
            180                 185                 190

Arg Glu Lys Gln His Leu Phe Asp Leu Ser Asp Lys Asp Ser Phe Phe
            195                 200                 205

Asp Ser Lys Thr Arg Ser Thr Ile Val Tyr Glu Ile Leu Lys Arg Thr
210                 215                 220

Thr Cys Thr Lys Ala Lys Tyr Ser Met Gly Ile Thr Ser Leu Leu Ala
225                 230                 235                 240

Asn Gly Val Tyr Ala Ala Ala Tyr Pro Leu His Asp Gly Asp Tyr Asn
                245                 250                 255

Gly Glu Asn Val Glu Phe Asn Asp Arg Lys Leu Leu Tyr Glu Glu Trp
            260                 265                 270

Ala Arg Tyr Gly Val Phe Tyr Lys Tyr Gln Pro Ile Asp Leu Val Arg
            275                 280                 285

Lys Tyr Phe Gly Glu Lys Ile Gly Leu Tyr Phe Ala Trp Leu Gly Val
            290                 295                 300

Tyr Thr Gln Met Leu Ile Pro Ala Ser Ile Val Gly Ile Ile Val Phe
305                 310                 315                 320

Leu Tyr Gly Cys Ala Thr Met Asp Glu Asn Ile Pro Ser Met Glu Met
                325                 330                 335

Cys Asp Gln Arg His Asn Ile Thr Met Cys Pro Leu Cys Asp Lys Thr
            340                 345                 350

Cys Ser Tyr Trp Lys Met Ser Ser Ala Cys Ala Thr Ala Arg Ala Ser
            355                 360                 365

His Leu Phe Asp Asn Pro Ala Thr Val Phe Phe Ser Val Phe Met Ala
            370                 375                 380

Leu Trp Ala Ala Thr Phe Met Glu His Trp Lys Arg Lys Gln Met Arg
385                 390                 395                 400

Leu Asn Tyr Arg Trp Asp Leu Thr Gly Phe Glu Glu Glu Glu Ala
                405                 410                 415

Val Lys Asp His Pro Arg Ala Glu Tyr Glu Ala Arg Val Leu Glu Lys
            420                 425                 430

Ser Leu Lys Lys Glu Ser Arg Asn Lys Glu Thr Asp Lys Val Lys Leu
            435                 440                 445

Thr Trp Arg Asp Arg Phe Pro Ala Tyr Leu Thr Asn Leu Val Ser Ile
450                 455                 460
```

```
Ile Phe Met Ile Ala Val Thr Phe Ala Ile Val Leu Gly Val Ile Ile
465                 470                 475                 480

Tyr Arg Ile Ser Met Ala Ala Leu Ala Met Asn Ser Ser Pro Ser
            485                 490                 495

Val Arg Ser Asn Ile Arg Val Thr Val Thr Ala Thr Ala Val Ile Ile
                500                 505                 510

Asn Leu Val Ile Ile Leu Leu Asp Glu Val Tyr Gly Cys Ile Ala
            515                 520                 525

Arg Trp Leu Thr Lys Ile Glu Val Pro Lys Thr Glu Lys Ser Phe Glu
530                 535                 540

Glu Arg Leu Ile Phe Lys Ala Phe Leu Leu Lys Phe Val Asn Ser Tyr
545                 550                 555                 560

Thr Pro Ile Phe Tyr Val Ala Phe Phe Lys Gly Arg Phe Val Gly Arg
                565                 570                 575

Pro Gly Asp Tyr Val Tyr Ile Phe Arg Ser Phe Arg Met Glu Glu Cys
            580                 585                 590

Ala Pro Gly Gly Cys Leu Met Glu Leu Cys Ile Gln Leu Ser Ile Ile
            595                 600                 605

Met Leu Gly Lys Gln Leu Ile Gln Asn Asn Leu Phe Glu Ile Gly Ile
610                 615                 620

Pro Lys Met Lys Lys Leu Ile Arg Tyr Leu Lys Leu Lys Gln Ser
625                 630                 635                 640

Pro Pro Asp His Glu Glu Cys Val Lys Arg Lys Gln Arg Tyr Glu Val
                645                 650                 655

Asp Tyr Asn Leu Glu Pro Phe Ala Gly Leu Thr Pro Glu Tyr Met Glu
            660                 665                 670

Met Ile Ile Gln Phe Gly Phe Val Thr Leu Phe Val Ala Ser Phe Pro
            675                 680                 685

Leu Ala Pro Leu Phe Ala Leu Leu Asn Asn Ile Ile Glu Ile Arg Leu
690                 695                 700

Asp Ala Lys Lys Phe Val Thr Glu Leu Arg Arg Pro Val Ala Val Arg
705                 710                 715                 720

Ala Lys Asp Ile Gly Ile Trp Tyr Asn Ile Leu Arg Gly Ile Gly Lys
                725                 730                 735

Leu Ala Val Ile Ile Asn Ala Phe Val Ile Ser Phe Thr Ser Asp Phe
            740                 745                 750

Ile Pro Arg Leu Val Tyr Leu Tyr Met Tyr Ser Lys Asn Gly Thr Met
            755                 760                 765

His Gly Phe Val Asn His Thr Leu Ser Ser Phe Asn Val Ser Asp Phe
            770                 775                 780

Gln Asn Gly Thr Ala Pro Asn Asp Pro Leu Asp Leu Gly Tyr Glu Val
785                 790                 795                 800

Gln Ile Cys Arg Tyr Lys Asp Tyr Arg Glu Pro Pro Trp Ser Glu Asn
                805                 810                 815

Lys Tyr Asp Ile Ser Lys Asp Phe Trp Ala Val Leu Ala Ala Arg Leu
            820                 825                 830

Ala Phe Val Ile Val Phe Gln Asn Leu Val Met Phe Met Ser Asp Phe
            835                 840                 845

Val Asp Trp Val Ile Pro Asp Ile Pro Lys Asp Ile Ser Gln Gln Ile
            850                 855                 860

His Lys Glu Lys Val Leu Met Val Glu Leu Phe Met Arg Glu Glu Gln
865                 870                 875                 880
```

```
Asp Lys Gln Gln Leu Leu Glu Thr Trp Met Glu Lys Glu Arg Gln Lys
            885                 890                 895

Asp Glu Pro Pro Cys Asn His His Asn Thr Lys Ala Cys Pro Asp Ser
        900                 905                 910

Leu Gly Ser Pro Ala Pro Ser His Ala Tyr His Gly Gly Val Leu
            915                 920                 925

<210> SEQ ID NO 2
<211> LENGTH: 2784
<212> TYPE: DNA
<213> ORGANISM: Homo sapiens

<400> SEQUENCE: 2
```

| | | | | |
|---|---|---|---|---|
| atgagggtca | acgagaagta | ctcgacgctc | ccggccgagg | accgcagcgt ccacatcatc | 60 |
| aacatctgcg | ccatcgagga | catcggctac | ctgccgtccg | agggcacgct gctgaactcc | 120 |
| ttatctgtgg | accctgatgc | cgagtgcaag | tatggcctgt | acttcaggga cggccggcgc | 180 |
| aaggtggact | acatcctggt | gtaccatcac | aagaggccct | cgggcaaccg gaccctggtc | 240 |
| aggagggtgc | agcacagcga | caccccctct | ggggctcgca | gcgtcaagca ggaccacccc | 300 |
| ctgccgggca | gggggcgtc | gctggatgca | ggctcagggg | agcccccgat ggactaccac | 360 |
| gaggatgaca | gcgcttccg | cagggaggag | tacgagggca | acctcctgga ggcgggcctg | 420 |
| gagctggagc | gggacgagga | catgtaccac | attaatgaga | cccgtggcct cctgaaaaaa | 480 |
| atcaactctg | tgctccagaa | aatcacagat | cccatccagc | ccaaagtggc tgagcacagg | 540 |
| ccccagacca | tgaagagact | ctcctatccc | ttctcccggg | agaagcagca tctatttgac | 600 |
| ttgtctgata | aggattcctt | tttcgacagc | aaaacccgga | gcacgattgt ctatgagatc | 660 |
| ttgaagagaa | cgacgtgtac | aaaggccaag | tacagcatgg | gcatcacgag cctgctggcc | 720 |
| aatggtgtgt | acgcggctgc | atacccactg | cacgatggag | actacaacgg tgaaaacgtc | 780 |
| gagttcaacg | acagaaaact | cctgtacgaa | gagtgggcac | gctatggagt tttctataag | 840 |
| taccagccca | tcgacctggt | caggaagtat | tttggggaga | gatcggcct gtacttcgcc | 900 |
| tggctgggcg | tgtacacccca | gatgctcatc | cctgcctcca | tcgtgggaat cattgtcttc | 960 |
| ctgtacggat | gcgccaccat | ggatgaaaac | atccccagca | tggagatgtg tgaccagaga | 1020 |
| cacaatatca | ccatgtgccc | gctttgcgac | aagacctgca | gctactggaa gatgagctca | 1080 |
| gcctgcgcca | cggcccgcgc | cagccacctc | ttcgacaacc | ccgccacggt cttcttctct | 1140 |
| gtcttcatgg | ccctctgggc | tgccaccttc | atggagcact | ggaagcggaa acagatgcga | 1200 |
| ctcaactacc | gctgggacct | cacgggcttt | gaagaggaag | aggaggctgt caaggatcat | 1260 |
| cctagagctg | aatacgaagc | cagagtcttg | gagaagtctc | tgaagaaaga gtccagaaac | 1320 |
| aaagagactg | caaagtgaa | gctgacatgg | agagatcggt | tcccagccta cctcactaac | 1380 |
| ttggtctcca | tcatcttcat | gattgcagtg | acgtttgcca | tcgtcctcgg cgtcatcatc | 1440 |
| tacaggatct | ccatggccgc | cgccttggcc | atgaactcct | cccctccgt gcggtccaac | 1500 |
| atccgggtca | cagtcacagc | caccgcggtc | atcatcaacc | tagtggtcat catcctcctg | 1560 |
| gacgaggtgt | atggctgcat | agcccgatgg | ctcaccaaga | tcgaggtccc aaagacggag | 1620 |
| aaaagctttg | aggagaggct | gatcttcaag | gctttcctgc | tgaagtttgt gaattcctac | 1680 |
| acccccatct | tttacgtggc | gttcttcaaa | ggccggtttg | ttggacgccc gggcgactac | 1740 |
| gtgtacattt | tccgttcctt | ccgaatggaa | gagtgtgcgc | caggggctg cctgatggag | 1800 |
| ctatgcatcc | agctcagcat | catcatgctg | gggaaacagc | tgatccagaa caacctgttc | 1860 |

-continued

```
gagatcggca tcccgaagat gaagaagctc atccgctacc tgaagctgaa gcagcagagc    1920
ccccctgacc acgaggagtg tgtgaagagg aaacagcggt acgaggtgga ttacaacctg    1980
gagcccttcg cgggcctcac cccagagtac atggaaatga tcatccagtt tggcttcgtc    2040
accctgtttg tcgcctcctt ccccctggcc ccactgtttg cgctgctgaa caacatcatc    2100
gagatccgcc tggacgccaa aaagtttgtc actgagctcc gaaggccggt agctgtcaga    2160
gccaaagaca tcggaatctg gtacaatatc ctcagaggca ttgggaagct tgctgtcatc    2220
atcaatgcct tcgtgatctc cttcacgtct gacttcatcc cgcgcctggt gtacctctac    2280
atgtacagta agaacgggac catgcacggc ttcgtcaacc acaccctctc ctccttcaac    2340
gtcagtgact tccagaacgg cacggccccc aatgaccccc tggacctggg ctacgaggtg    2400
cagatctgca ggtataaaga ctaccgagag ccgccgtggt cggaaaacaa gtacgacatc    2460
tccaaggact tctgggccgt cctggcagcc cggctggcgt ttgtcatcgt cttccagaac    2520
ctggtcatgt tcatgagcga ctttgtggac tgggtcatcc cggacatccc caaggacatc    2580
agccagcaga tccacaagga aaggtgctc atggtggagc tgttcatgcg ggaggagcaa    2640
gacaagcagc agctgctgga aacctggatg gagaaggagc ggcagaagga cgagccgccg    2700
tgcaaccacc acaacaccaa agcctgccca gacagcctcg gcagcccagc ccccagccat    2760
gcctaccacg ggggcgtcct gtag                                          2784
```

<210> SEQ ID NO 3
<211> LENGTH: 239
<212> TYPE: PRT
<213> ORGANISM: Artificial sequence
<220> FEATURE:
<223> OTHER INFORMATION: /note="Description of artificial sequence: hsYFP"

<400> SEQUENCE: 3

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser Gln Asn Val Tyr Leu Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 4
<211> LENGTH: 720
<212> TYPE: DNA
<213> ORGANISM: Artificial sequence
<220> FEATURE:
<223> OTHER INFORMATION: /note="Description of artificial sequence: hsYFP"

<400> SEQUENCE: 4
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagct gatctgcacc accggcaagc tgcccgtgcc ctggcccacc   180
ctcgtgacca ccttcggcta cggcctgaag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccagaac gtctatctga tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaagtga   720

<210> SEQ ID NO 5
<211> LENGTH: 20
<212> TYPE: DNA
<213> ORGANISM: Artificial sequence
<220> FEATURE:
<223> OTHER INFORMATION: /note="Description of artificial sequence: TMEM16A forward primer"

<400> SEQUENCE: 5
ggccacgatg agggtcaacg                                                 20

<210> SEQ ID NO 6
<211> LENGTH: 20
<212> TYPE: DNA
<213> ORGANISM: Artificial sequence
<220> FEATURE:
<223> OTHER INFORMATION: /note="Description of artificial sequence: TMEM16A reverse primer"

<400> SEQUENCE: 6
cctgtagcta tgccagcggg                                                 20

<210> SEQ ID NO 7
<211> LENGTH: 10
<212> TYPE: DNA
<213> ORGANISM: Artificial sequence
<220> FEATURE:
<223> OTHER INFORMATION: /note="Description of artificial sequence: ATG translation start codon"

```
<400> SEQUENCE: 7
gccaccatgg                                                            10

<210> SEQ ID NO 8
<211> LENGTH: 15
<212> TYPE: DNA
<213> ORGANISM: Artificial sequence
<220> FEATURE:
<223> OTHER INFORMATION: /note="Description of artificial sequence:
      Oligonucleotide TMEM16A"

<400> SEQUENCE: 8
ggaaacagcg gtacg                                                      15

<210> SEQ ID NO 9
<211> LENGTH: 15
<212> TYPE: DNA
<213> ORGANISM: Artificial sequence
<220> FEATURE:
<223> OTHER INFORMATION: /note="Description of artificial sequence:
      Oligonucleotide TMEM16A"

<400> SEQUENCE: 9
gcgggatgaa gtcag                                                      15

<210> SEQ ID NO 10
<211> LENGTH: 20
<212> TYPE: DNA
<213> ORGANISM: Artificial sequence
<220> FEATURE:
<223> OTHER INFORMATION: /note="Description of artificial sequence:
      Oligonucleotide exon-3 forward"

<400> SEQUENCE: 10
gatgccgagt gcaagtatgg                                                 20

<210> SEQ ID NO 11
<211> LENGTH: 20
<212> TYPE: DNA
<213> ORGANISM: Artificial sequence
<220> FEATURE:
<223> OTHER INFORMATION: /note="Description of artificial sequence:
      Oligonucleotide exon-3 reverse"

<400> SEQUENCE: 11
tttgggctgg atgggatctg                                                 20

<210> SEQ ID NO 12
<211> LENGTH: 20
<212> TYPE: DNA
<213> ORGANISM: Artificial sequence
<220> FEATURE:
<223> OTHER INFORMATION: /note="Description of artificial sequence:
      Oligonucleotide exon-15 forward"

<400> SEQUENCE: 12
acgaagccag agtcttggag                                                 20

<210> SEQ ID NO 13
<211> LENGTH: 20
<212> TYPE: DNA
<213> ORGANISM: Artificial sequence
<220> FEATURE:
```

```
<223> OTHER INFORMATION: /note="Description of artificial sequence:
      Oligonucleotide exon-15 reverse"

<400> SEQUENCE: 13
caaacttcag caggaaagcc                                              20
```